(12) United States Patent
Geβner et al.

(10) Patent No.: US 9,444,058 B2
(45) Date of Patent: Sep. 13, 2016

(54) PREPARATION OF PI-EXTENDED NAPHTHALENE DIIMIDES AND THEIR USE AS SEMICONDUCTOR

(71) Applicant: BASF SE, Ludwigshafen (DE)

(72) Inventors: Thomas Geβner, Heidelberg (DE); Sabin-Lucian Suraru, Seattle, WA (US); Frank Würthner, Höchberg (DE)

(73) Assignee: BASF SE (DE)

( * ) Notice: Subject to any disclaimer, the term of this patent is extended or adjusted under 35 U.S.C. 154(b) by 0 days.

(21) Appl. No.: 14/786,024

(22) PCT Filed: Apr. 22, 2014

(86) PCT No.: PCT/IB2014/060902
§ 371 (c)(1),
(2) Date: Oct. 21, 2015

(87) PCT Pub. No.: WO2014/174435
PCT Pub. Date: Oct. 30, 2014

(65) Prior Publication Data
US 2016/0104846 A1 Apr. 14, 2016

(30) Foreign Application Priority Data

Apr. 25, 2013 (EP) .................... 13165368

(51) Int. Cl.
| | |
|---|---|
| *C07D 471/22* | (2006.01) |
| *H01L 29/772* | (2006.01) |
| *H01L 51/00* | (2006.01) |
| *C07D 491/22* | (2006.01) |
| *C09B 5/62* | (2006.01) |
| *C09B 23/01* | (2006.01) |
| *C09B 23/04* | (2006.01) |
| *H01G 9/20* | (2006.01) |
| *H01L 51/05* | (2006.01) |

(52) U.S. Cl.
CPC ......... *H01L 51/0072* (2013.01); *C07D 471/22* (2013.01); *C07D 491/22* (2013.01); *C09B 5/62* (2013.01); *C09B 23/0058* (2013.01); *C09B 23/04* (2013.01); *H01G 9/2059* (2013.01); *H01L 51/0053* (2013.01); *H01L 51/0071* (2013.01); *H01L 51/0508* (2013.01); *Y02E 10/542* (2013.01)

(58) Field of Classification Search
USPC ................. 546/32, 31, 41; 313/504
See application file for complete search history.

(56) References Cited

U.S. PATENT DOCUMENTS 8,309,728 B2   11/2012 Koenemann
2012/0253045 A1  10/2012 Gao et al.

FOREIGN PATENT DOCUMENTS

| CN | 101693719 A | 4/2010 |
|---|---|---|
| CN | 101885732 A | 11/2010 |
| WO | WO-2007074137 A1 | 7/2007 |
| WO | WO-2010052287 A1 | 5/2010 |

OTHER PUBLICATIONS

Suraru, S-L. et al.: Diindole-annulated naphthalene diimides: synthesis and optical and electronic properties of syn-and anti-isomers. J. Org. Chem., vol. 79, pp. 128-139, 2014.*

Hu et al., "Core-Expanded Naphthalene Diimides Fused with Sulfur Heterocycles and End-Capped with Electron-Withdrawing Groups for Air-Stable Solution-Processed n-Channel Organic Thin Film Transistors", *Chemistry of Materials*, vol. 23, pp. 1204-1215 (2011).

Suraru et al., "A core-extended naphthalene diimide as a p-channel semiconductor", *Chem. Commun.*, vol. 47, No. 41, pp. 11504-11506 (2011).

(Continued)

*Primary Examiner* — Charanjit Aulakh

(74) *Attorney, Agent, or Firm* — Drinker Biddle & Reath LLP

(57) ABSTRACT

The present invention provides the compounds of formulae

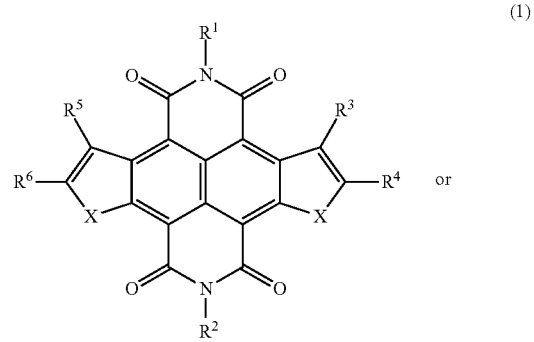

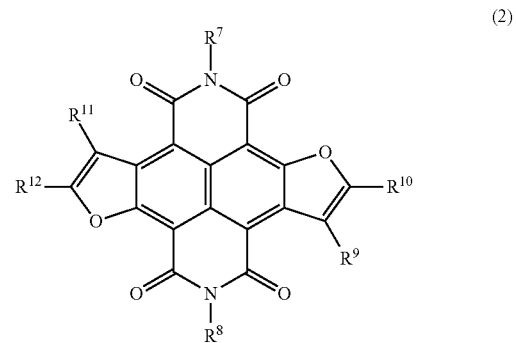

and electronic devices comprising these compounds.

14 Claims, No Drawings

(56) References Cited

OTHER PUBLICATIONS

Chen et al., "Dithiazole-fused naphthalene diimides toward new n-type semiconductors", *Journal of Materials Chemistry C*, vol. 1, pp. 1087-1092 (2013).

International Search Report for PCT/IB2014/060902 mailed Jan. 28, 2015.

* cited by examiner

PREPARATION OF PI-EXTENDED NAPHTHALENE DIIMIDES AND THEIR USE AS SEMICONDUCTOR

CROSS-REFERENCE TO RELATED APPLICATIONS

This application is a national stage application (under 35 U.S.C. §371) of PCT/IB2014/060902, filed Apr. 22, 2014, which claims benefit of European Application No. 13165368.5, filed Apr. 25, 2013, both of which are incorporated herein by reference in their entirety.

The present invention relates to core-extended naphthalene diimide derivatives, and to electronic devices comprising the core-extended naphthalene diimide derivatives as semiconducting material.

Naphthalene diimides are a versatile class of chromophores. Naphthalene diimides also gain more and more interest in applications such as in organic field-effect transistors, organic light emitting devices, photovoltaic devices such as dye-sensitized solar cells (DSCs), and xerography.

It is known to modify the properties of naphthalene diimides by functionalization of the parent naphthalene diimide core at the 2, 3, 6 and 7 positions. However, lateral core expansion of naphthalene diimides has only been demonstrated recently.

Suraru, S.-L.; Zhieschang, U.; Klauk, H.; Warthner, F. Chem. Commun. 2011, 47, 11504-11506 describes the following core-extended naphthalene diimide and its use as p-channel semiconductor in thin film transistors:

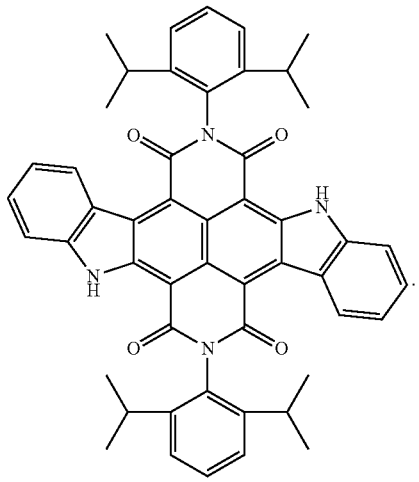 [SMILES: CC(C)c1cccc(C(C)C)c1N1C(=O)c2c3[nH]c4ccccc4c3c3c4c(c5[nH]c6ccccc6c5c(c24)C1=O)C(=O)N(c1c(C(C)C)cccc1C(C)C)C3=O]

Hu, Y.; Gao, X.; Di, C.; Yang, X.; Zhang, F.; Liu, Y.; U. H. and Zhu, D. Chem. Mater. 2011, 23, 1204-1215 describes the following core-expanded naphthalene diimides fused with sulfur heterocycles and their use as n-channel semiconductors in thin film transistors:

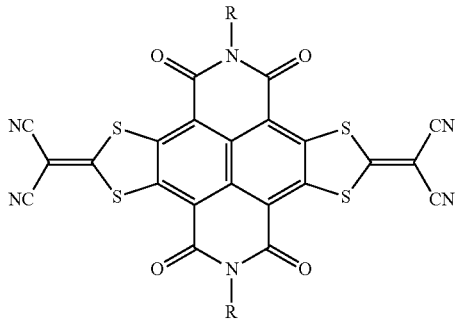

1: R = 2-decyltetradecy
2: R = 2-octyldodecyl
3: R = 2-hexyldecyl
4: R = 2-hexyloctyl
5: R = 2-butyloctyl
6: R = 3-hexylundecyl
7: R = 4-hexyldodecyl

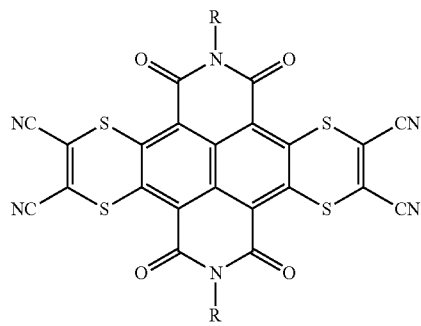

8: R = 2-decyltetradecy
9: R = 2-octyldodecyl

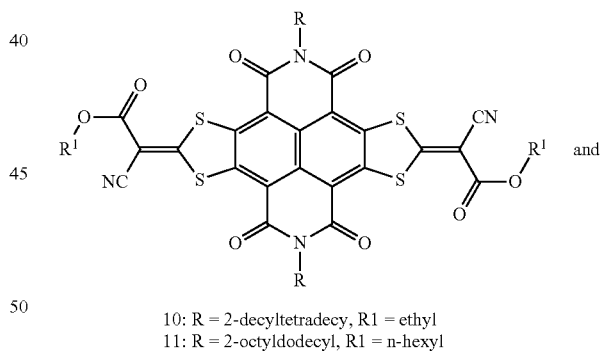

10: R = 2-decyltetradecy, R1 = ethyl
11: R = 2-octyldodecyl, R1 = n-hexyl

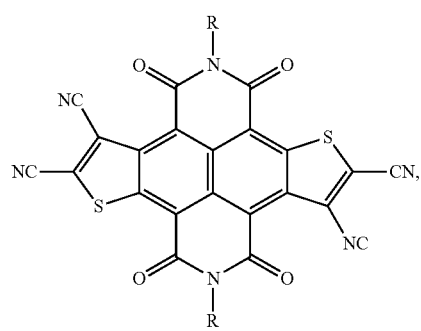

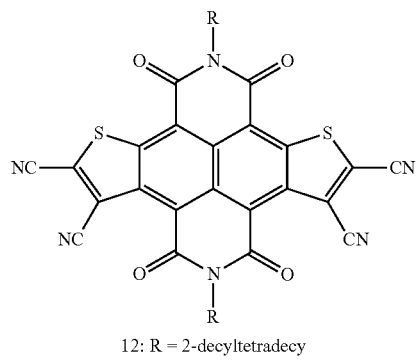
12: R = 2-decyltetradecy
Doria, F.; Di Antonio, M.; Benotti, M.; Verga, D.; Freccero, M. *J. Org. Chem.* 2009, 74, 8616-8625 describes the following naphthalene diimide derivatives:
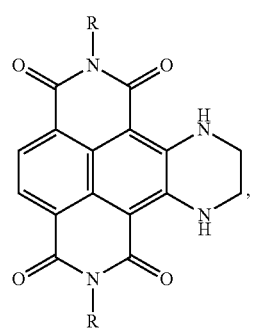 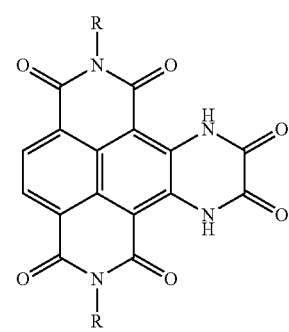
4a: R = —(CH$_2$)$_4$CH$_3$   5a: R = —(CH$_2$)$_4$CH$_3$
4b: R = —CH(CH$_2$)$_5$        5b: R = —CH(CH$_2$)$_5$
Langhals, H.; Kinzel, S. *J. Org. Chem.* 2010, 75, 7781-7784 describes naphthalene diimide derivatives:
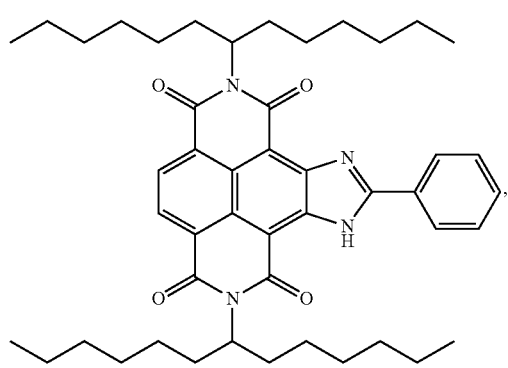
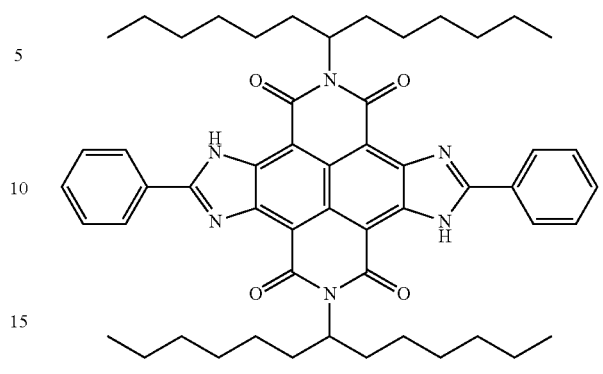
3a
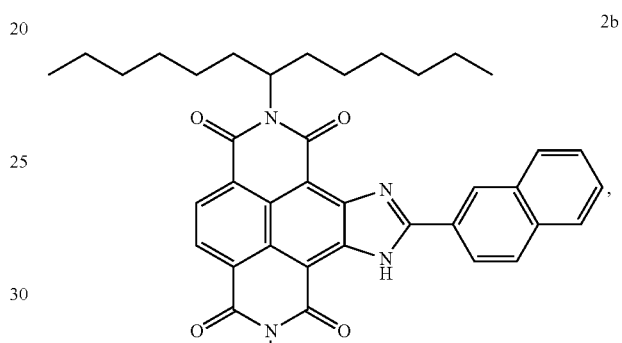
2b
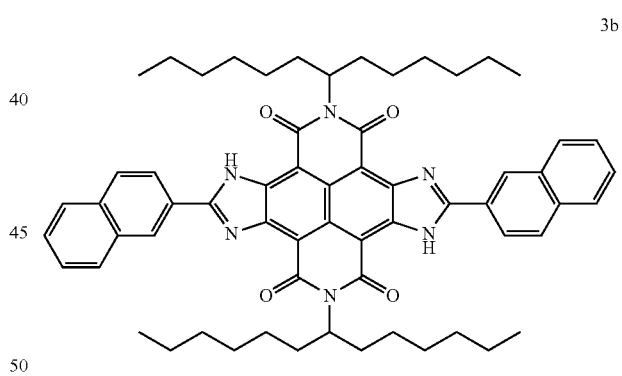
3b
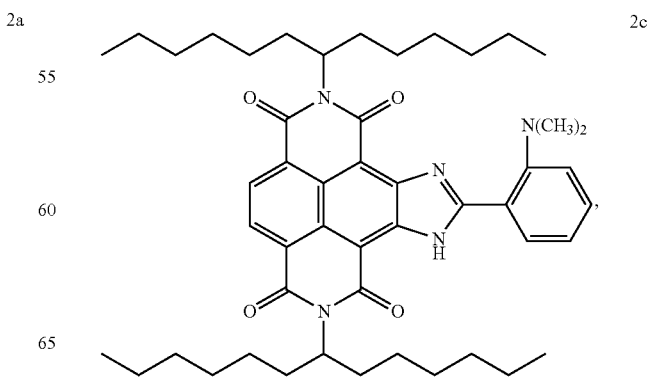
2c 3c

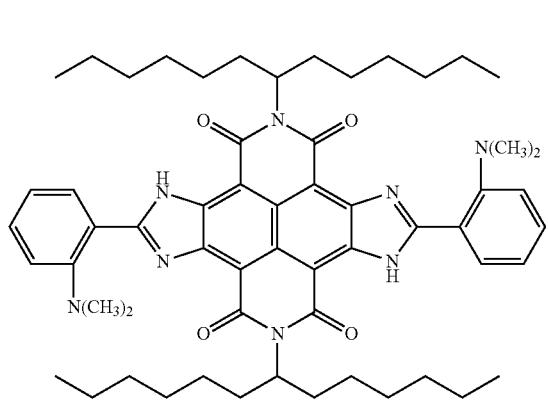

Zhou, C.; Li, Y.; Zhao, Y.; Zhang, J.; Yang, W.; Li, Y. *Org. Lett.* 2011, 13, 292-295 describes the following core-substituted naphthalenediimide compound:

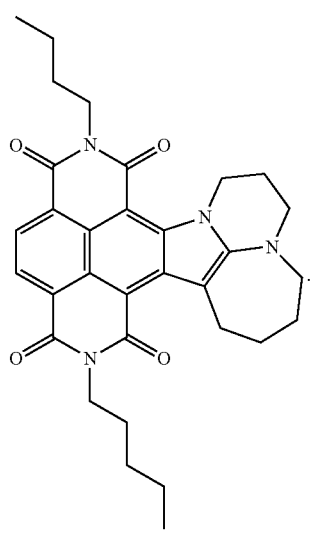 [SMILES: CCCCCN1C(=O)c2ccc3c4c(c5c(c6c7n5CCCN7CCCC6)c(c24)C1=O)C(=O)N(CCCC)C3=O]

Chen, X.; Guo, Y.; Tan, L.; Yang, G.; Li, Y.; Zhang, G.; Liu, Z.; Xu, W.; Zhang, D. *J. Mat. Chem. C,* 2013, 1, 1087-1092 describes the following compounds and their use as n-channel semiconductors in organic field effect transistors:

1

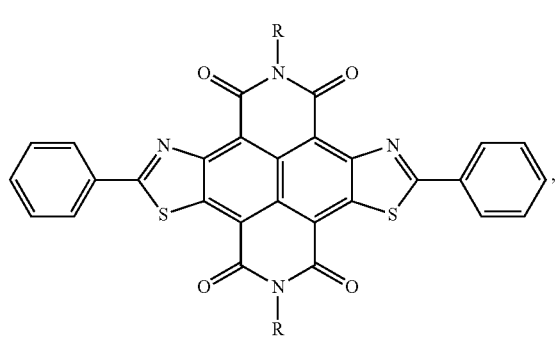

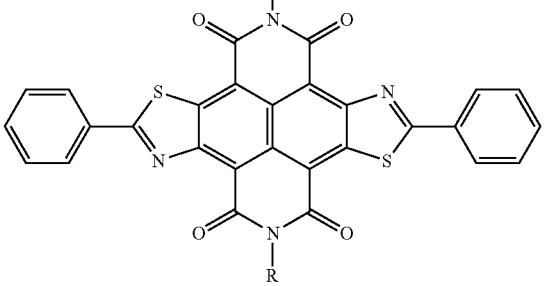

R = octyldodecyl

2

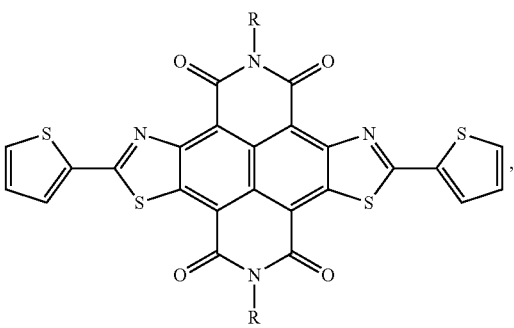

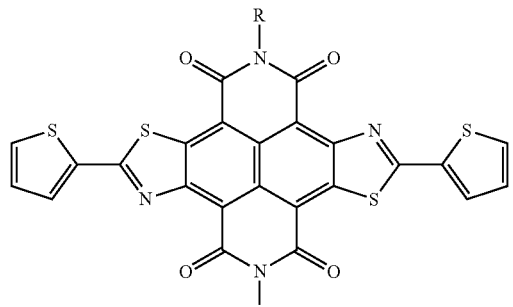

R = octyldodecyl

It was the object of the present invention to provide core-substituted naphthalene diimide derivatives.

This object is solved by the compounds of claim 1, and the device of claim 5.

The compounds of the present invention are of formulae (1)

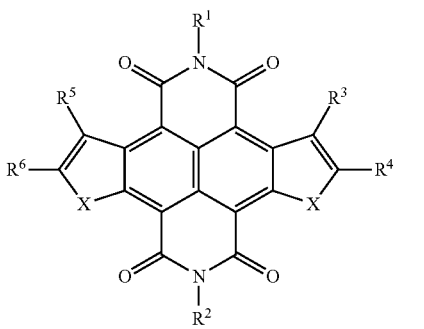 or

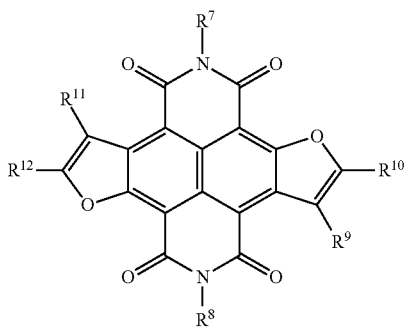

(2)

wherein
X is O or NR$^{13}$,
  wherein R$^{13}$ is H, C$_{1-30}$-alkyl, C$_{3-8}$-cycloalkyl, C$_{6-14}$-aryl or a 5 to 14 membered heterocyclic system A,
R$^1$, R$^2$, R$^7$ and R$^8$ are independently from each other H, C$_{1-30}$-alkyl, C$_{3-8}$-cycloalkyl, C$_{6-14}$-aryl or a 5 to 14 membered heterocyclic system A, and
R$^3$, R$^4$, R$^5$, R$^6$, R$^9$, R$^{10}$, R$^{11}$ and R$^{12}$ are independently from each other H, C$_{1-30}$-alkyl, C$_{3-8}$-cycloalkyl, C$_{6-14}$-aryl, a 5 to 14 membered heterocyclic system A, halogen, NR$^{14}$R$^{15}$, OH, OR$^{16}$, SH, SR$^{17}$, CN, NO$_2$, —S—CN, —C(O)—H, —C(O)—R$^{18}$, COOH, —C(O)—NR$^{19}$R$^{20}$, —SO$_2$—OH, —SO$_2$—NH$_2$ or —SO$_2$—R$^{21}$, wherein
  R$^{14}$, R$^{15}$, R$^{16}$, R$^{17}$, R$^{18}$, R$^{19}$, R$^{20}$ and R$^{21}$ are independently from each other H, C$_{1-30}$-alkyl, C$_{3-8}$-cycloalkyl, C$_{6-14}$-aryl or a 5 to 14 membered heterocyclic system A,
or
R$^3$ and R$^4$,
R$^5$ and R$^6$,
R$^9$ and R$^{10}$, or
R$^{11}$ and R$^{12}$
together with the C-atoms, to which they are attached, form a C$_{5-14}$-membered ring system or a 5 to 14 membered heterocyclic system B,
wherein
  C$_{1-30}$-alkyl may be substituted with one or more substituents selected from the group consisting of —O—C$_{1-10}$-alkyl, —[—O—C$_{1-6}$-alkylene-]$_n$-O—C$_{1-10}$-alkyl, phenyl, cyclopentyl, cyclohexyl, halogen, —C(O)O—R$^{22}$, —O—C(O)—R$^{23}$ and C(O)—R$^{24}$,
  C$_{3-8}$-cycloalkyl may be substituted with one or more substituents selected from the group consisting of C$_{1-10}$-alkyl, —O—C$_{1-10}$-alkyl, —[—O—C$_{1-6}$-alkylene-]$_n$-O—C$_{1-10}$-alkyl and phenyl,
  C$_{6-14}$-aryl, the C$_{5-14}$-membered ring system, the 5 to 14 membered heterocyclic system A and the 5 to 14 membered heterocyclic system B may be substituted with one or more substituents selected from the group consisting of C$_{1-10}$-alkyl, —O—C$_{1-10}$-alkyl, —[—O—C$_{1-6}$-alkylene-]$_n$-O—C$_{1-10}$-cyclopentyl, cyclohexyl, phenyl, halogen, CN, NO$_2$, —S—CN, —C(O)—H, —C(O)O—R$^{22}$, —O—C(O)—R$^{23}$ and C(O)—R$^{24}$,
  wherein
    C$_{1-10}$-alkyl may be substituted with one or more halogen,
    R$^{22}$, R$^{23}$ and R$^{24}$ are independently from each other C$_{1-10}$-alkyl, cyclopentyl, cyclohexyl or phenyl, and
  n is 1 to 15.
C$_{1-10}$-alkyl, C$_{1-30}$-alkyl and C$_{1-20}$-alkyl can be branched or unbranched. Examples of C$_{1-10}$-alkyl are methyl, ethyl, n-propyl, isopropyl, n-butyl, sec-butyl, isobutyl, tert-butyl, n-pentyl, neopentyl, isopentyl, n-(1-ethyl)propyl, n-hexyl, n-heptyl, n-octyl, n-(2-ethyl)hexyl, n-nonyl and n-decyl. Examples of C$_{1-20}$-alkyl are C$_{1-10}$-alkyl and n-undecyl, n-dodecyl, n-tridecyl, n-tetradecyl, n-pentadecyl, n-hexadecyl, n-heptadecyl, n-octadecyl, n-nonadecyl and n-icosyl (C$_{20}$). Examples of C$_{1-30}$-alkyl are C$_{1-20}$-alkyl and n-(2-octyl)dodecyl, n-docosyl (C$_{22}$), n-tetracosyl (C$_{24}$), n-(2-decyl)tetradecyl, n-hexacosyl (C$_{26}$), n-octacosyl (C$_{28}$) and n-triacontyl (C$_{30}$).

Examples of C$_{3-8}$-cycloalkyl are cyclopropyl, cyclobutyl, cyclopentyl, cycloexyl, cycloheptyl and cyclooctyl.

The 5 to 14 membered heterocyclic system A can be a saturated 5 to 14 membered heterocyclic system A or an unsaturated 5 to 14 membered heterocyclic system A including an aromatic 5 to 14 membered heterocyclic system A. The 5 to 14 membered heterocyclic system A includes one or more heteroatoms. The heteroatoms are preferably N, O and/or S. The 5 to 14 membered heterocyclic system A can be monocyclic or polycyclic such as dicyclic.

Examples of 5 to 8 membered saturated heterocyclic systems A are

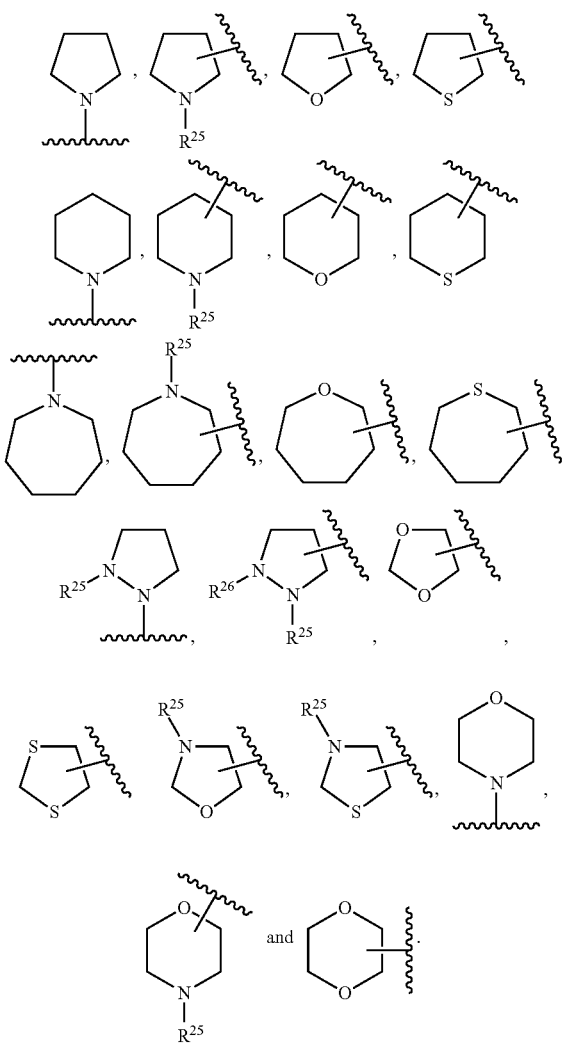

Examples of unsaturated 5 to 14 membered heterocyclic systems A are

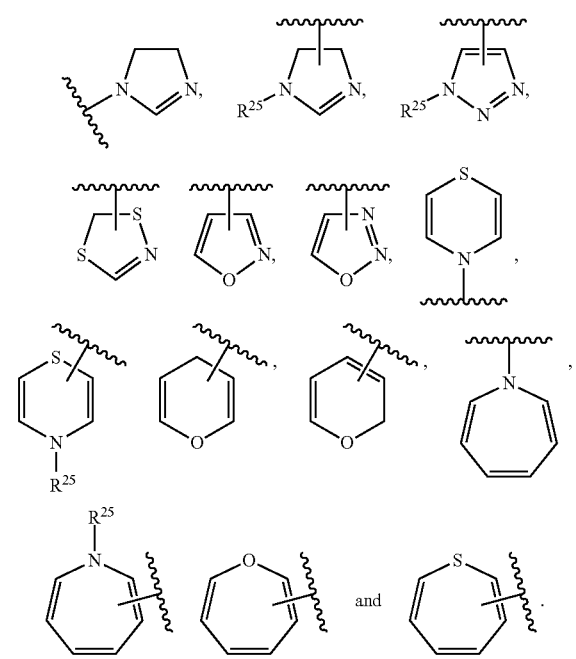

as well as aromatic 5 to 14 membered heterocyclic systems A such as

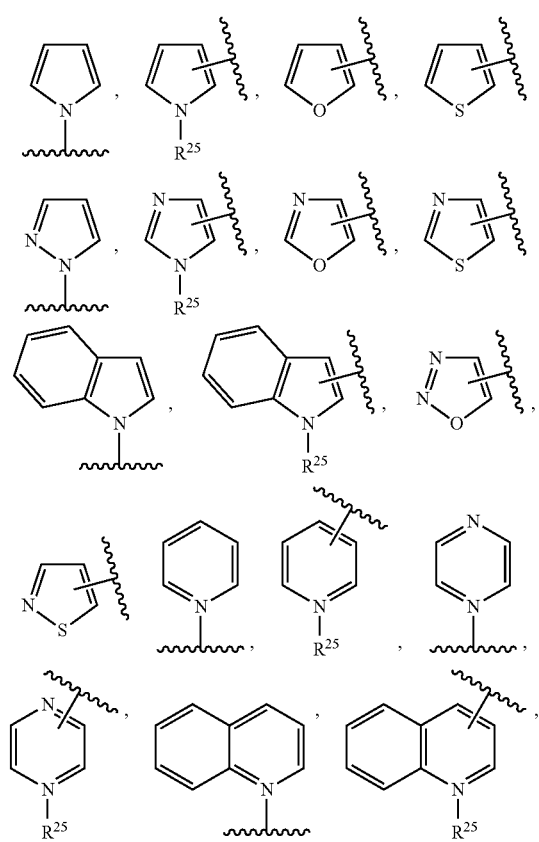

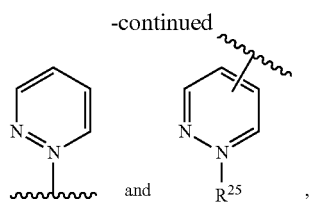

Examples of $C_{6-14}$-aryl are phenyl and naphthyl.
Examples of halogen are F, Cl, Br and I.
The $C_{5-14}$-membered ring systems can be monocyclic or polycyclic such as dicyclic.
Examples of $C_{5-14}$-membered ring systems are

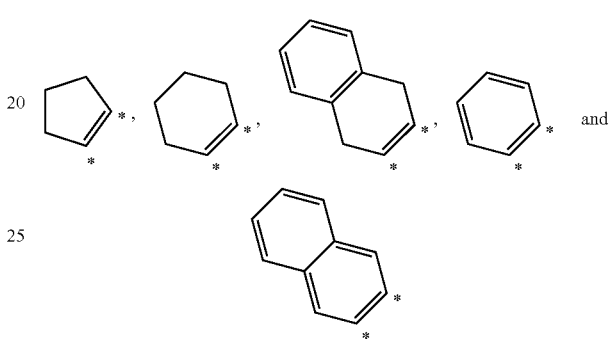

wherein the C-atoms marked with a star are the C-atoms to which $R^3$ and $R^4$, $R^5$ and $R^6$, $R^9$ and $R^{10}$, or $R^{11}$ and $R^{12}$ are attached.

The 5 to 14 membered heterocyclic system B can be monocyclic or polycyclic such as dicyclic. The 5 to 14 membered heterocyclic system B includes one or more heteroatoms. The heteroatoms are preferably N, O and/or S. Examples 5 to 14 membered heterocyclic systems B are

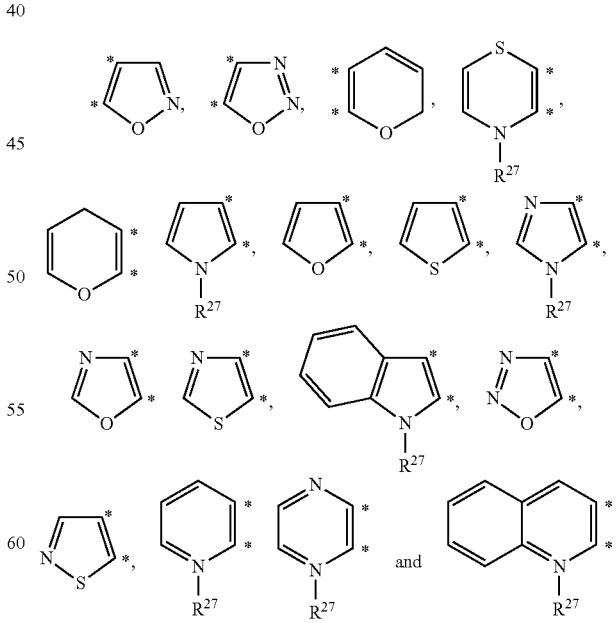

wherein the C-atoms marked with a star are the C-atoms to which $R^3$ and $R^4$, $R^5$ and $R^6$, $R^9$ and $R^{10}$, or $R^{11}$ and $R^{12}$ are attached.

Examples of $C_{1-6}$-alkylene are methylene, ethylene, propylene and butylene.

In preferred compounds of formulae (1) or (2)

X is O or $NR^{13}$,
  wherein $R^{13}$ is H or $C_{1-30}$-alkyl,
$R^1$, $R^2$, $R^7$ and $R^8$ are independently from each other H, $C_{1-30}$-alkyl or $C_{6-14}$-aryl, and
$R^3$ and $R^4$,
$R^5$ and $R^6$,
$R^9$ and $R^{10}$, or
$R^{11}$ and $R^{12}$
together with the C-atoms, to which they are attached, form a $C_{5-14}$-membered ring system or a 5 to 14 membered heterocyclic system B,
wherein
  $C_{1-30}$-alkyl may be substituted with one or more substituents selected from the group consisting of —O—$C_{1-10}$-alkyl, —[—O—$C_{1-6}$-alkylene-]$_n$-O—$C_{1-10}$-alkyl, phenyl, cyclopentyl, cyclohexyl, halogen, —C(O)O—$R^{22}$, —O—C(O)—$R^{23}$ and C(O)—$R^{24}$,
  $C_{6-14}$-aryl, the $C_{5-14}$-membered ring system and the 5 to 14 membered heterocyclic system B may be substituted with one or more substituents selected from the group consisting of $C_{1-10}$-alkyl, —O—$C_{1-10}$-alkyl, —[—O—$C_{1-6}$-alkylene-]$_n$-O—$C_{1-10}$-alkyl, cyclopentyl, cyclohexyl, phenyl, halogen, CN, $NO_2$, —S—CN, —C(O)—H, —C(O)O—$R^{22}$, —O—C(O)—$R^{23}$ and C(O)—$R^{24}$,
  wherein
    $C_{1-10}$-alkyl may be substituted with one or more halogen,
    $R^{22}$, $R^{23}$ and $R^{24}$ are independently from each other $C_{1-10}$-alkyl, cyclopentyl, cyclohexyl or phenyl, and
    n is 1 to 15.

In more preferred compounds of formulae (1) or (2)

X is O or $NR^{13}$,
  wherein $R^{13}$ is H,
$R^1$, $R^2$, $R^7$ and $R^8$ are independently from each other $C_{1-20}$-alkyl or $C_{6-14}$-aryl, and
$R^3$ and $R^4$,
$R^5$ and $R^6$,
$R^9$ and $R^{10}$, or
$R^{11}$ and $R^{12}$
together with the C-atoms, to which they are attached, form a $C_{5-14}$-membered ring system
wherein
  $C_{1-20}$-alkyl may be substituted with one or more substituents selected from the group consisting of —O—$C_{1-10}$-alkyl, —[—O—$C_{1-6}$-alkylene-]$_n$-O—$C_{1-10}$-alkyl, phenyl, cyclopentyl, cyclohexyl, halogen, —C(O)O—$R^{22}$, —O—C(O)—$R^{23}$ and C(O)—$R^{24}$,
  $C_{6-14}$-aryl and the $C_{5-14}$-membered ring system may be substituted with one or more substituents selected from the group consisting of $C_{1-10}$-alkyl, —O—$C_{1-10}$-alkyl, —[—O—$C_{1-6}$-alkylene-]$_n$-O—$C_{1-10}$-alkyl, cyclopentyl, cyclohexyl, phenyl, halogen, CN, $NO_2$, —S—CN, —C(O)—H, —C(O)O—$R^{22}$, —O—C(O)—$R^{23}$ and C(O)—$R^{24}$,
  wherein
    $C_{1-10}$-alkyl may be substituted with one or more halogen,
    $R^{22}$, $R^{23}$ and $R^{24}$ are independently from each other $C_{1-10}$-alkyl, cyclopentyl, cyclohexyl or phenyl, and
    n is 1 to 15.

In most preferred compounds of formulae (1) or (2)

X is O or $NR^{13}$,
  wherein $R^{13}$ is H,
$R^1$, $R^2$, $R^7$ and $R^8$ are independently from each other $C_{1-20}$-alkyl or $C_{6-14}$-aryl, and
$R^3$ and $R^4$,
$R^5$ and $R^6$,
$R^9$ and $R^{10}$, or
$R^{11}$ and $R^{12}$
together with the C-atoms, to which they are attached, form a $C_{5-14}$-membered ring system selected from the group consisting of

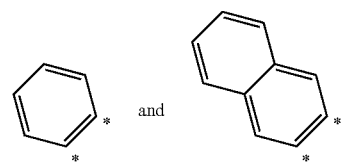 [SMILES: c1ccccc1 ; c1ccc2ccccc2c1]

wherein the C-atoms marked with a star are the C-atoms to which $R^3$ and $R^4$, $R^5$ and $R^6$, $R^9$ and $R^{10}$, or $R^{11}$ and $R^{12}$ are attached,
wherein
  $C_{6-14}$-aryl and the $C_{5-14}$-membered ring system selected from the group consisting of

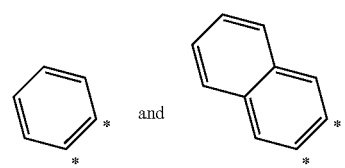

may be substituted with one or more substituents selected from the group consisting of $C_{1-10}$-alkyl, which may be substituted with one or more halogen, and halogen.

Particular preferred compounds of formulae (1) are the compounds of formulae

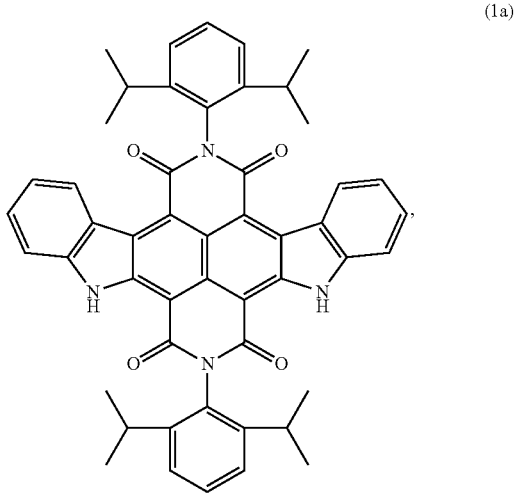

(1a)

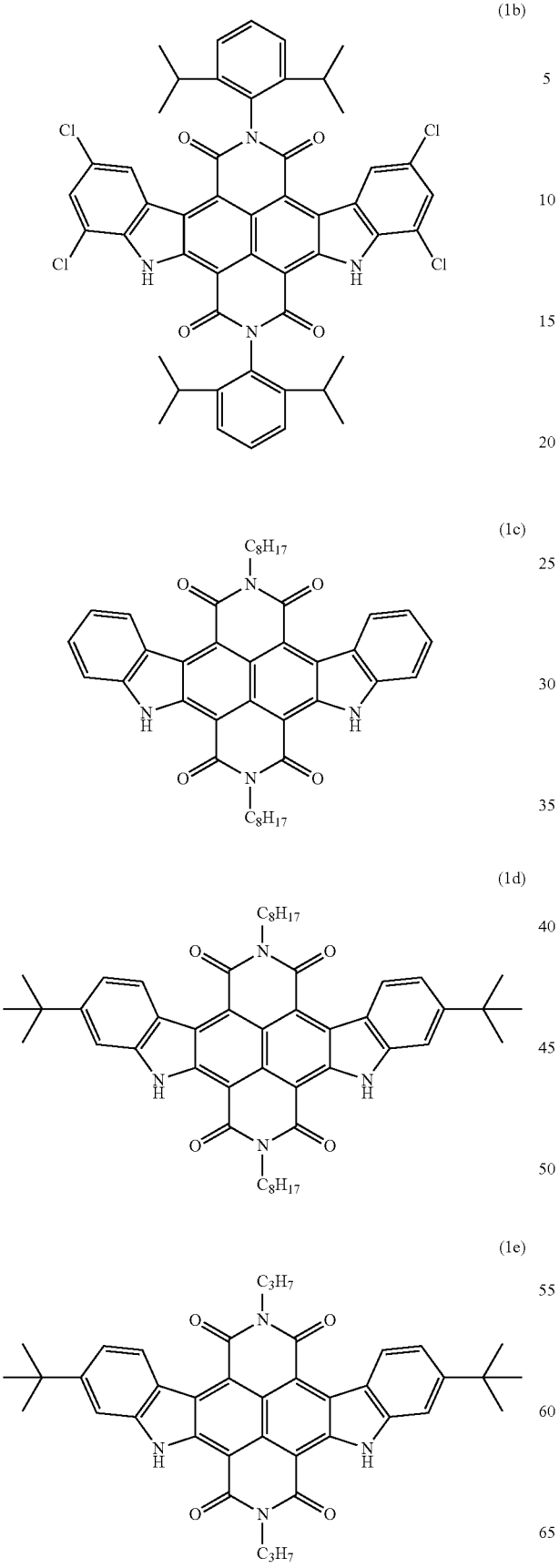
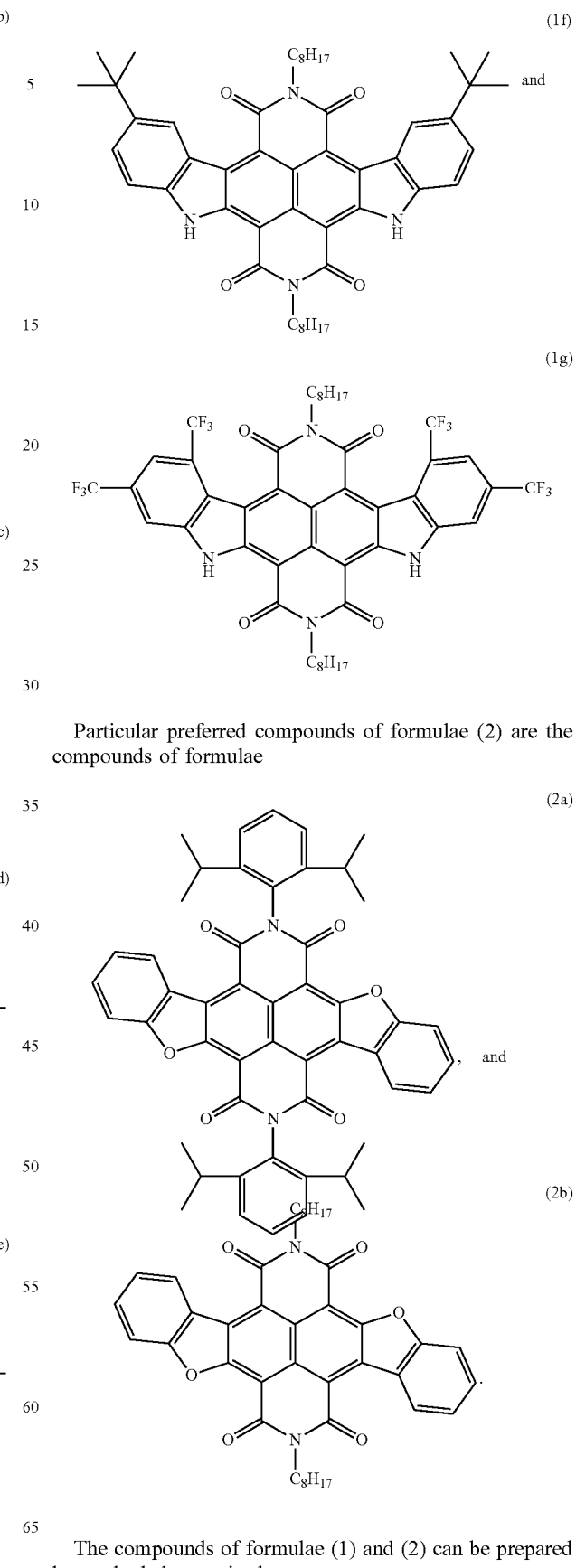
Particular preferred compounds of formulae (2) are the compounds of formulae
The compounds of formulae (1) and (2) can be prepared by methods known in the art.

For example, the compound of formula (1)

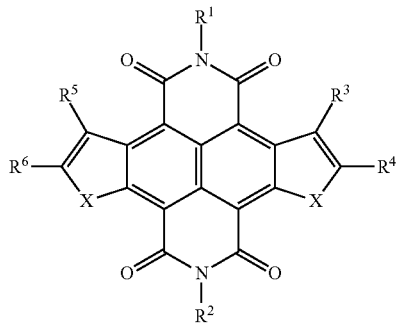
(1)

wherein
X is O or NR$^{13}$,
  wherein R$^{13}$ is H.
R$^1$ and R$^2$ are independently from each other C$_{1-20}$-alkyl or C$_{6-14}$-aryl, and
R$^3$ and R$^4$, or
R$^5$ and R$^6$,
together with the C-atoms, to which they are attached, form a C$_{5-14}$-membered ring system selected from the group consisting of

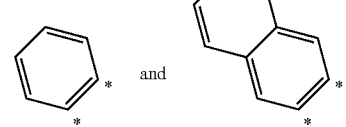

wherein the C-atoms marked with a star are the C-atoms to which R$^3$ and R$^4$, or, R$^5$ and R$^6$ are attached,
wherein
C$_{6-14}$-aryl and the C$_{5-14}$-membered ring system selected from the group consisting of

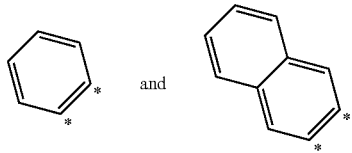

may be substituted with one or more C$_{1-10}$-alkyl, which may be substituted with one or more halogen, or with halogen, may be prepared by
(i) reacting a compound of formula

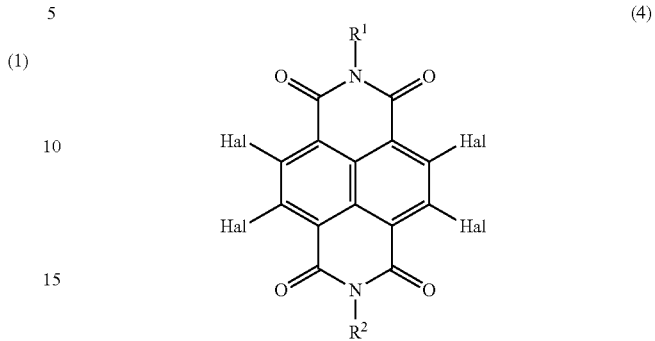
(4)

wherein R$^1$ and R$^2$ are as depicted for formula (1) and Hal is halogen,
with

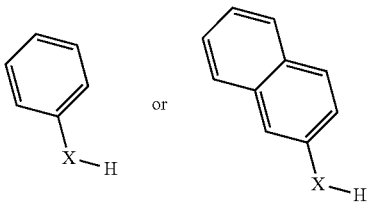

in order to obtain a compound of formula

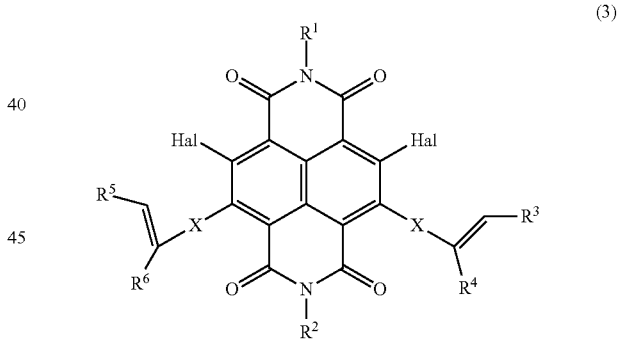
(3)

wherein R$^1$, R$^2$, R$^3$, R$^4$, R$^5$ and R$^6$ are as depicted for formula (1) and Hal is halogen, and (ii) reacting the compound of formula (3) obtained in the first step with a metal catalyst A in order to obtain the compound of formula (1).

The first step of the process or the preparation of a compound of formula (1) is usually performed in a suitable organic solvent such as chloroform. The first step of the process is usually performed at an elevated temperature, for example at a temperature of 40 to 100° C., preferably at a temperature of 50 to 80° C.

The metal catalyst A of the second step of the process for the preparation of a compound of formula (1) is usually a transition metal catalyst. Preferably, it is a Pd-catalyst such as Pd(OAc)$_2$. The metal catalyst of the second step of the process is usually used in the presence of a base and a suitable solvent. The solvent can be a suitable organic solvent such as DMF. The base can be suitable base such as $K_2CO_3$. The second step of the process is usually performed at an elevated temperature, for example at a temperature of 50 to 200° C., preferably at a temperature of 80 to 120° C.

The preparation of compounds of formula (4) is described WO 2007/074137, or in X. Gao et al., *Org. Lett.* 2007, 9, 3917-3920.

For example, a compound of formula (2)

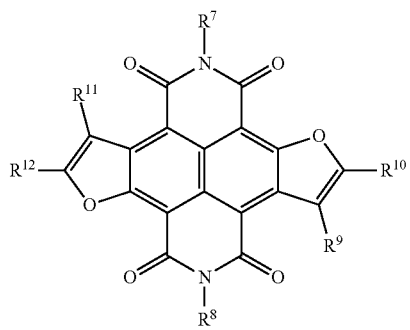

(2)

wherein
$R^7$ and $R^8$ are independently from each other $C_{1-20}$-alkyl or $C_{6-14}$-aryl, and
$R^9$ and $R^{10}$, or
$R^{11}$ and $R^{12}$
together with the C-atoms, to which they are attached, form a $C_{5-14}$-membered ring system selected from the group consisting of

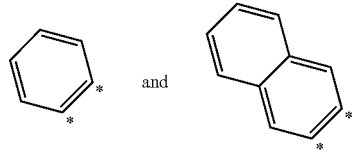 [SMILES: c1ccccc1 ; c1ccc2ccccc2c1]

wherein the C-atoms marked with a star are the C-atoms to which $R^9$ and $R^{10}$, or, $R^{11}$ and $R^{12}$ are attached,
wherein
$C_{6-14}$-aryl and the $C_{5-14}$-membered ring system selected from the group consisting of

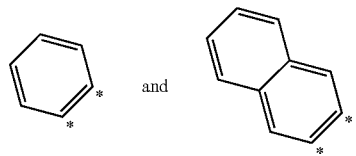

may be substituted with one or more $C_{1-10}$-alkyl, may be prepared by reacting a compound of formula

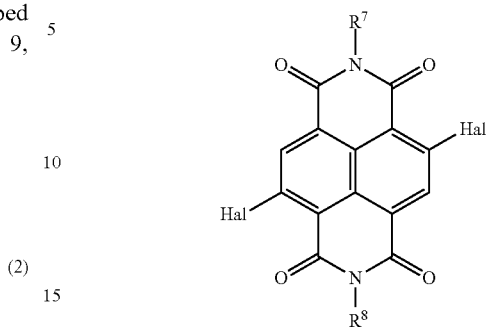

(5)

wherein $R^7$ and $R^8$ are as depicted for formula (1) and Hal is halogen,
with a metal catalyst B and a compound of formula

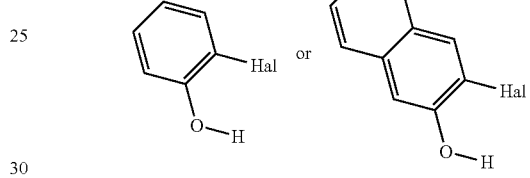

wherein Hal is halogen
in order to obtain a compound of formula (2).

The metal catalyst B of the second step of the process for the preparation of a compound of formula (2) is usually a transition metal catalyst. Preferably, it is a Pd-catalyst such as $Pd(OAc)_2$, The metal catalyst of the second step of the process is usually used in the presence of a base and a suitable solvent. The solvent can be a suitable organic solvent such as DMF. The base can be suitable base such as $K_2CO_3$. The second step of the process is usually performed at an elevated temperature, for example at a temperature of 50 to 200° C., preferably at a temperature of 100 to 160° C.

The preparation of compounds of formula (5) is described in Chopin, S.; Chaignon, F. C.; Blart, E.; Odobel, F. *J. Mater. Chem.* 2007, 17, 4139-4146.

Also part of the invention is an electronic device comprising the compounds of the present invention as semiconducting material.

The electronic device can be any electronic device, for example an organic photovoltaic (OPV) cell, an organic field-effect transistor (OFET) or an organic light emitting diode (OLED). Preferably, the electronic device is an organic field-effect transistor.

Usually, an organic field effect transistor comprises a dielectric layer, a semiconducting layer and a substrate. In addition, an organic field effect transistor usually comprises a gate electrode and source/drain electrodes.

An organic field effect transistor can have various designs, for example bottom-gate design or top-gate design.

The substrate can be any suitable substrate such as undoped or highly doped silicon, for example in form of a silicon waver, or glass, or a plastic substrate such as polyethersulfone, polycarbonate, polysulfone, polyethylene terephthalate (PET) and polyethylene naphthalate (PEN).

The dielectric layer comprises a dielectric material. The dielectric material can be any suitable material such as aluminium oxide, aluminium oxide in combination with a self-assembled monolayer (SAM) of a phosphonic acid such as $C_{14}H_{29}PO(OH)_2$ [TDPA] or $C_7F_{15}C_{11}H_{22}PO(OH)_2$ [FODPA]), silicon dioxide, or an organic polymer such as polystyrene (PS), poly(methyl-methacrylate) (PMMA), poly (4-vinylphenol) (PVP), poly(vinyl alcohol) (PVA), benzocyclobutene (BCB) or polyimide (PI), or a combination of these materials The dielectric layer can have a thickness of 5 to 2000 nm, preferably of 5 to 500 nm, more preferably of 5 to 100 nm.

The semiconducting layer comprises one or more of the compounds of the present invention. The semiconducting layer can have a thickness of 5 to 500 nm, preferably of 10 to 100 nm, more preferably of 20 to 50 nm.

The source/drain electrodes can be made from any suitable source/drain material, for example silver (Ag), gold (Au) or tantalum (Ta). The source/drain electrodes can have a thickness of 1 to 100 nm, preferably from 5 to 50 nm.

The gate electrode can be made from any suitable gate material such as highly doped silicon, aluminium (Al), tungsten (W), indium tin oxide, silver (Ag), gold (Au) or tantalum (Ta), or from a combination of these materials. The gate electrode can have a thickness of 1 to 200 nm, preferably from 5 to 100 nm.

The field effect transistor can be prepared by methods known in the art.

For example, a bottom-gate organic field effect transistor can be prepared as follows:

Aluminium can be deposited on highly doped silicon wafers by thermal evaporation, followed by oxidation of the aluminium layer to aluminium oxide and treatment of the aluminium oxide surface with a phosphonic acid in order to form a self-assembled monolayer (SAM-layer) of the phosphonic acid on the aluminium oxide surface. The semiconducting material can be deposited on the SAM-layer by thermal sublimation. The source and drain electrodes can be formed by evaporating gold through a shadow mask. The back side of the highly doped silicon wafers can be coated with silver ink to serve as the gate electrode.

For example, a bottom-gate organic field effect transistor can be prepared as follows:

Aluminiumoxide can be deposited on highly doped silicon wafers with a thermally grown silicon dioxide layer by atomic layer deposition, followed by treatment of the aluminium oxide surface with a phosphonic acid in order to form a self-assembled monolayer (SAM-layer) of the phosphonic acid on the aluminium oxide surface. The semiconducting material can be deposited on the SAM-layer by thermal sublimation. The source and drain electrodes can be formed by evaporating gold through a shadow mask. The back side of the highly doped silicon wafers can coated be with silver ink to serve as the gate electrode.

Also part of the invention is the use of the compounds of the present invention as semiconducting materials.

The compounds of the present invention show a high stability, in particular towards oxidation, under ambient conditions. Organic devices, in particular organic field effect transistors, comprising compounds of the present invention as semiconducting material show high charge carrier mobilities and high on/off ratios.

EXAMPLES

Example 1

Preparation of Compound 1a

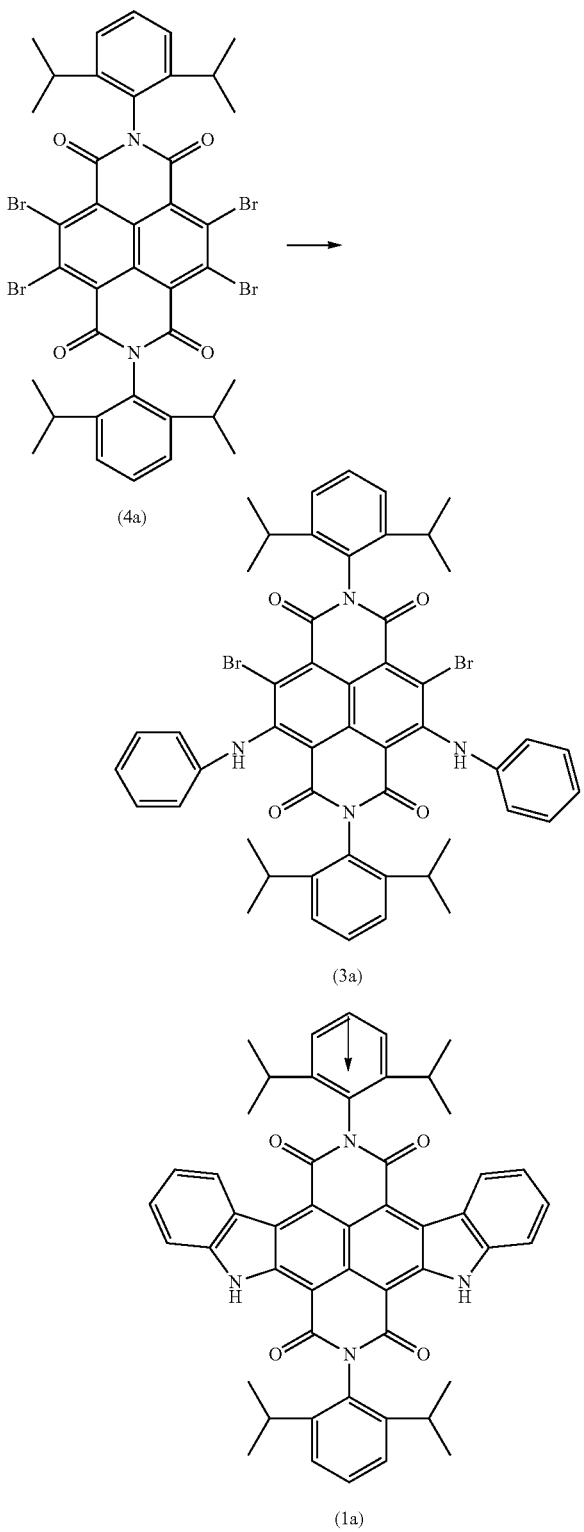

Preparation of Compound 4a

Compound 4a is prepared as described in example 9 of WO 2007/074137.

Preparation of Compound 3a

Aniline (1.8 mL) is added to a solution of compound 4a (149 mg, 0.146 mmol) in chloroform (50 mL). The solution is heated under reflux for 40 min. The solvent is removed under reduced pressure, and the remainder is purified by column chromatography (dichloromethane/pentane 1:1). A violet solid is obtained (162 mg, 82%). $^1$H NMR (400 MHz, CD$_2$Cl$_2$): 11.84 (s, 2H, NH) 7.53-7.47 (m, 2H), 7.37-7.31 (m, 8H), 7.16 (t, $^3$J=7.6 Hz, 2H), 7.07 (d, $^3$J=7.6 Hz, 4H), 2.77 (sept, $^3$J=6.8 Hz, 2H), 2.65 (sept, $^3$J=6.8 Hz, 2H), 1.18 (d, $^3$J=6.8 Hz, 12H), 1.11 (d, $^3$J=6.8 Hz, 12H). $^{13}$C NMR (100 MHz, CD$_2$Cl$_2$): 165.3, 161.7, 151.6, 146.3, 146.1, 141.9, 131.3, 131.0, 130.2, 129.5, 128.5, 125.1, 124.64, 124.56, 122.1, 119.8, 119.0, 108.3, 29.8, 29.6, 24.1, 24.0. MS (MALDI, neg-mode). found: 926.2 [M$^-$].

Preparation of Compound 1a

Dry DMF (5 mL) is added to a mixture of compound 3a (76.2 mg, 0.0822 mmol), K$_2$CO$_3$ (22.8 mg, 0.165 mmol) und Pd(OAc)$_2$ (5.4 mg, 26 μmol) under argon. The reaction mixture is stirred at 100° C. for 60 min. After cooling of the reaction mixture to room temperature, the solvent is removed under vacuo. The residue is purified by column chromatography (dichloromethane/pentane 1/1) yielding a dark red solid (20.8 mg, 33%). $^1$H NMR (400 MHz, CD$_2$Cl$_2$): δ=11.4 (s, 2H), 9.57 (dd, $^3$J=8.16 Hz, $^4$J=0.76 Hz, 2H), 7.73-7.66 (m, 4H), 7.66-7.57 (m, 2H), 7.49 (d, $^3$J=7.6 Hz, 2H), 7.46 (d, $^3$J=7.6 Hz, 2H), 7.41-7.37 (m, 2H), 2.98 (sept, $^3$J=6.8 Hz, 2H), 2.87 (sept, $^3$J=6.8 Hz, 2H), 1.22 (d, $^3$J=6.8 Hz, 12H), 1.20 (d, $^3$J=6.8 Hz, 12H). $^{13}$C NMR (100 MHz, CD$_2$Cl$_2$): δ=166.0, 164.9, 146.71, 146.66, 144.5, 144.1, 132.0, 131.0, 130.9, 130.20, 130.15, 130.0, 128.8, 125.8, 124.8, 124.6, 122.5, 122.1, 121.6, 118.8, 111.8, 103.3, 29.8, 29.7, 24.2, 24.1. HRMS (ESI, acetonitrile/CHCl$_3$ 1:1, pos-mode): calcd for C$_{50}$H$_{45}$N$_4$O$_4$ 765.3435. Found 765.3437.

Example 2

Preparation of Compound 2a

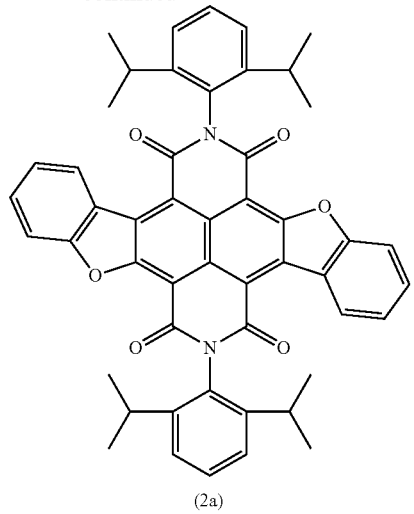

(2a)

DMF (15 mL) is added to a mixture of compound 5a (200 mg, 0.268 mmol), prepared as described in Chopin, S.; Chaignon, F. C.; Blart, E.; Odobel, F. J. Mater. Chem. 2007, 17, 4139-4146, 2-bromophenol (0.08 mL, 0.75 mmol), Pd(OAc)$_2$ (18.0 mg, 80.6 μmol) and K$_2$CO$_3$ (74.0 mg, 0.537 mmol) under argon. The reaction mixture is heated to reflux under argon for 3 hours. The solvent is removed under reduced pressure. The residue is purified by column chromatography (dichloromethane/pentane 2/1). The first fraction obtained is suspended in chloroform, heated to reflux and filtrated after being cooled to room temperature. The so-obtained residue is a light yellow solid (73.0 mg, 35%). $^1$H NMR (400 MHz, CD$_2$Cl$_2$): δ=9.53 (ddd, $^3$J=8.3 Hz, $^4$J=1.4 Hz, $^5$J=0.6 Hz, 2H), 7.81 (ddd, $^3$J=8.5 Hz, $^4$J=1.2 Hz, $^5$J=0.6 Hz, 2H), 7.84-7.79 (m, 2H), 7.61 (t, $^3$J=7.7 Hz, 2H), 7.56-7.50 (m, 2H), 7.46 (d, $^3$J=7.7 Hz, 4H), 2.89 (sept, $^3$J=6.8 Hz, 4H), 1.22 (d, $^3$J=6.84 Hz, 12H), 1.19 (d, $^3$J=6.84 Hz, 12H). MS (MALDI, pos-mode): 766.3 [M$^+$].

Example 3

Preparation of Compound 1 b

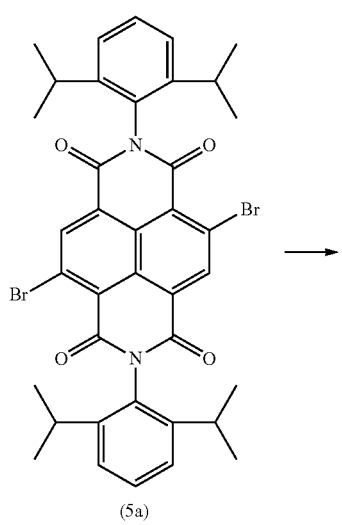

(5a)

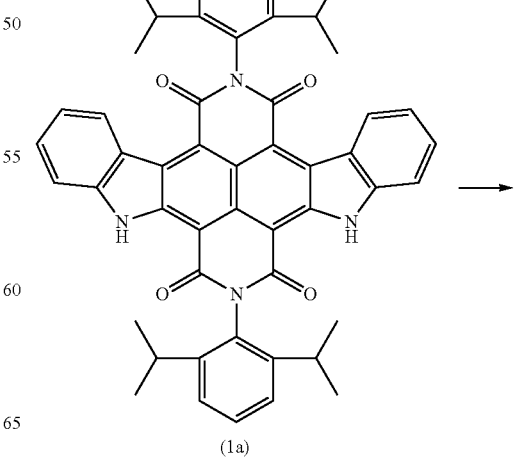

(1a)

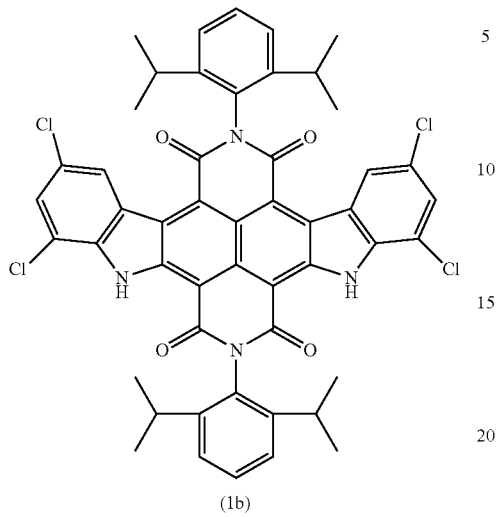

(1b)

A mixture of compound 1a (53.5 mg, 69.9 µmol), prepared as described in example 1, N-chlorosuccinimide (40.0 mg, 0.300 mmol), chloroform (8 mL) and acetonitrile (10 mL) is heated to reflux. After 3 days additional N-chlorosuccinimide (120 mg, 0.90 mmol) is added to the reaction mixture. After additional 8 hours, the solvent is removed under reduced pressure. The residue is purified by column chromatography and HPLC (dichloromethane/pentane 1:1) to yield compound 1b as a dark red solid (25 mg, 40%). $^1$H NMR (400 MHz, CD$_2$Cl$_2$) δ=11.55 (s, 2H), 9.55 (dd, $^4$J=1.8 Hz, $^5$J=0.5 Hz, 2H), 7.75 ($^4$J=1.8 Hz, 2H), 7.65 (t, $^3$J=7.5 Hz, 1H), 7.61 (t, $^3$J=7.5 Hz, 1H), 7.55-7.42 (m, 4H), 2.91 (sept, $^3$J=6.8 Hz, 2H), 2.84 (sept, $^3$J=6.8 Hz, 2H), 1.22 (t, $^3$J=6.8 Hz, 2H), 1.21 (t, $^3$J=&8 Hz, 2H). HRMS (ESI, positive, acetonitrile/CHCl$_3$ 1:1): calculated for C$_{50}$H$_{41}$Cl$_4$N$_4$O$_4$ 901.1877. Found 901.1881.

Example 4

Preparation of Compound 1c

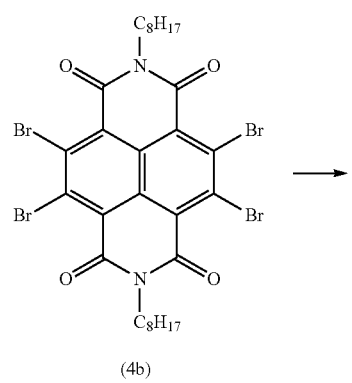

(4b)

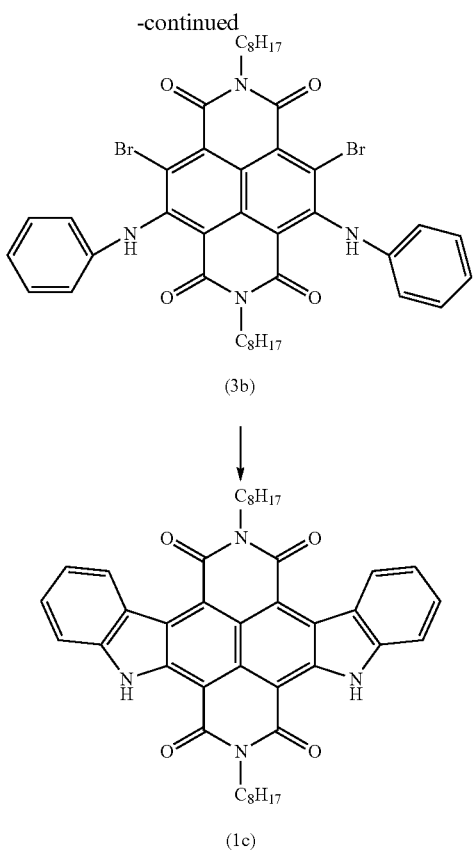

(3b)

↓

(1c)

Preparation of Compound 4b

Compound 4b is prepared as described in X. Gao et al., Org. Lett. 2007, 9, 3917-3920.

Preparation of Compound 3b

Aniline (1.8 mL) is added to a solution of compound 4b (170 mg, 0.211 mmol) in chloroform (50 mL). The solution is heated under reflux for 2 h. The solvent is removed under reduced pressure, and the residue is purified by column chromatography (dichloromethane/pentane 1:1). A violet solid is obtained (153 mg, 87%). $^1$H NMR (400 MHz, CD$_2$Cl$_2$): 11.88 (s, 2H, NH) 7.40-7.30 (m, 4H), 7.20-7.12 (m, 2H), 7.08-7.00 (m, 4H), 4.19 (t, $^3$J=7.7 Hz, 2H), 4.12 (t, $^3$J=7.7 Hz, 2H), 1.79-1.64 (m, 4H), 1.47-1.20 (m, 20H), 0.93-0.80 (m, 6H)

Preparation of Compound 1c

Dry DMF (10 mL) is added to a mixture of compound 3b (153 mg, 0.184 mmol), K$_2$CO$_3$ (102 mg, 0.738 mmol) und Pd(OAc)$_2$ (14 mg, 62 µmol) under argon. The reaction mixture is stirred at 100° C. for 80 min. After cooling of the reaction mixture to room temperature, the solvent is removed under vacuo. The residue is purified by column chromatography (dichloromethane/pentane 1/1) yielding a dark red solid (35 mg, 28%). $^1$H NMR (400 MHz, CD$_2$Cl$_2$): 11.11 (s, 2H, NH), 9.52 (d, $^3$J=8.6 Hz, 2H), 7.60-7.52 (m, 2H), 7.41 (d, $^3$J=7.8 Hz, 2H), 7.39-7.33 (m, 2H), 4.39-4.19 (m, 4H), 1.92-1.77 (m, 4H), 1.48-1.22 (m, 16H), 0.93-0.84 (m, 6H). MS (MALDI, pos-mode): 668.3 [M$^+$].

Example 5

Preparation of Compound 1d

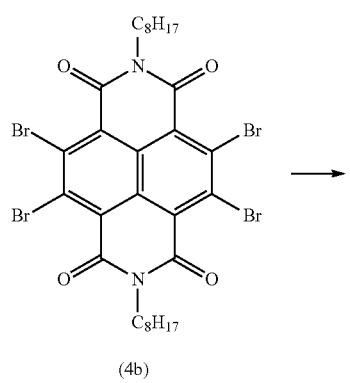
(4b)

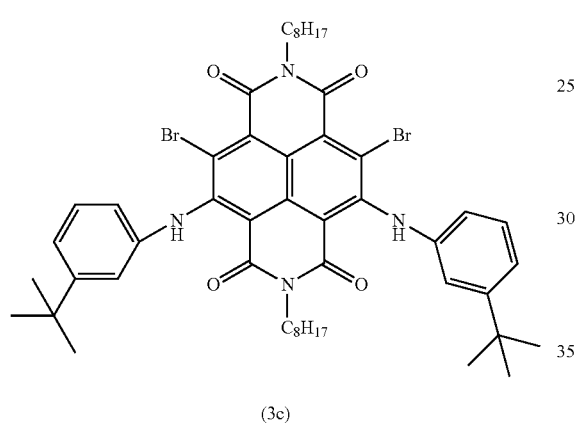
(3c)

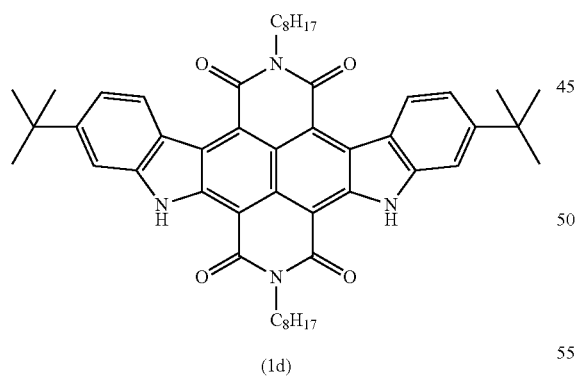
(1d)

Preparation of compound 3c 3-tert-Butylaniline (0.2 mL, 1.26 mmol) is added to a solution of compound 4b (144 mg, 0.179 mmol) in chloroform (10 mL). The solution is heated under reflux for 45 min. The solvent is removed under reduced pressure, and the residue is purified by column chromatography (dichloromethane/pentane 1/1). A violet solid is obtained (129 mg, 76%). $^1$H NMR (400 MHz, CDCl$_3$): 12.09 (s, 2H, NH), 7.25 (dd, $^3J$=7.8 Hz), 7.18 (ddd, $^3J$=7.8 Hz, $^4J$=1.6 Hz, $^4J$=1.0 Hz), 7.07 (dd, $^4J$=1.8 Hz), 6.82 (ddd, $^3J$=7.8 Hz, $^4J$=2.2 Hz, $^4J$=1.0 Hz), 4.20 (t, $^3J$=7.7 Hz, 2H), 4.15 (t, $^3J$=7.7 Hz, 2H), 1.79-1.67 (m, 4H), 1.47-1.17 (m, 38H), 0.90-0.82 (m, 6H).

Preparation of Compound 1d

Dry DMF (7 mL) is added to a mixture of compound 3c (99 mg, 0.105 mmol), K$_2$CO$_3$ (29 mg, 0.210 mmol) and Pd(OAc)$_2$ (7.0 mg, 31 μmol) under argon. The reaction mixture is stirred at 100° C. for 60 min. After cooling of the reaction mixture to room temperature, the solvent is removed under vacuo. The residue is purified by column chromatography (dichloromethane/pentane 1/1) yielding a dark red solid. $^1$H NMR (400 MHz, CD$_2$Cl$_2$): 11.12 (s, 2H, NH), 9.45 (d, $^3J$=8.7 Hz, 2H), 7.58 (d, $^4J$=1.4 Hz, 2H), 7.49 (dd, $^3J$=8.7 Hz, $^4J$=1.4 Hz, 2H), 4.13-4.02 (m, 4H), 1.82-1.68 (m, 4H), 1.52 (s, 9H), 1.50-1.24 (m, 18H), 0.93-0.84 (m, 6H).

Example 6

Preparation of Compound 1e

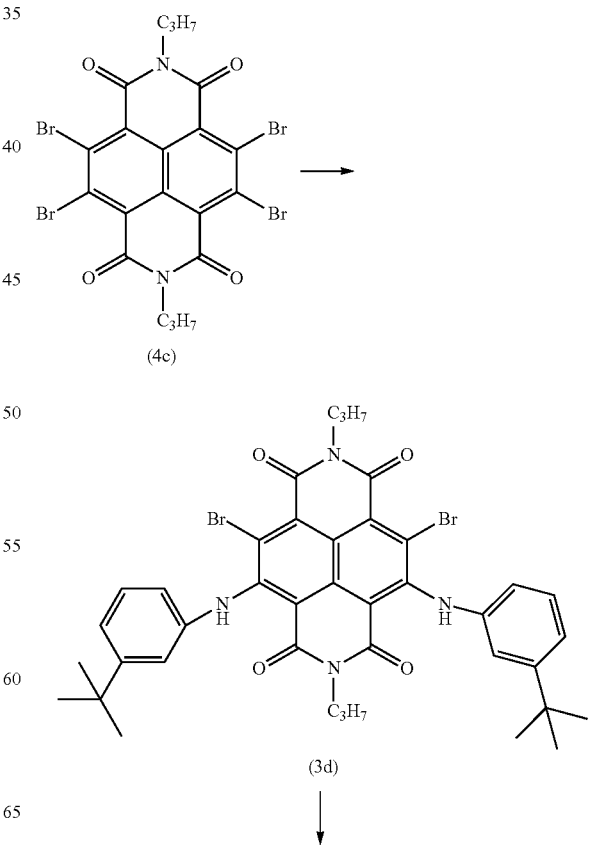
(4c)

(3d)

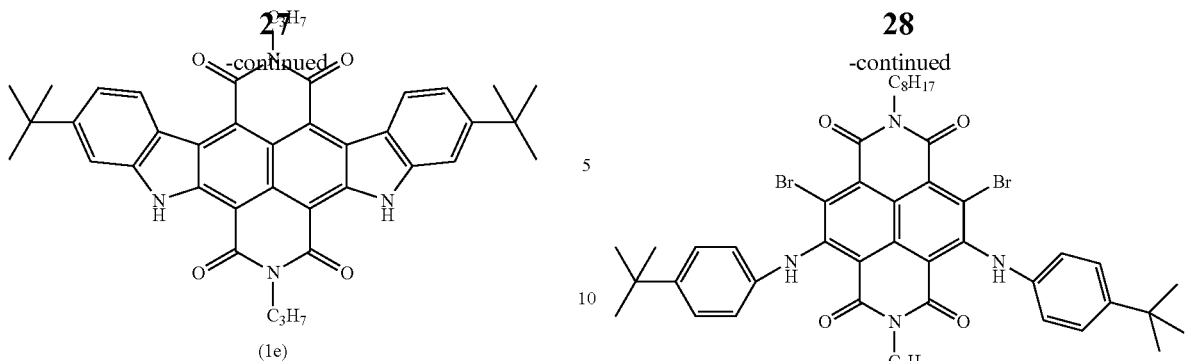

(1e)

Preparation of Compound 4c

Compound 4c is prepared in analogy to compound 4b as described in example 4.

Preparation of Compound 3d 3-tert-Butylaniline (0.14 mL, 0.88 mmol) is added to a solution of compound 4b (81.1 mg, 0.122 mmol) in chloroform (10 mL). The solution is heated under reflux for 2 h. The solvent is removed under reduced pressure, and the residue is purified by column chromatography (dichloromethane/pentane 4:1). A violet solid is obtained (88 mg, 87%). $^1$H NMR (400 MHz, CDCl$_3$): 12.1 (s, 2H), 7.25 (t, $^3$J=7.8 Hz, 2H), 7.18 (d, $^3$J=7.8 Hz, 2H), 7.07 (t, $^4$J=2.0 Hz, 2H), 6.83 (d, $^3$J=8.0 Hz, 2H), 4.24-4.16 (m, 2H), 4.16-4.08 (m, 2H) (m, 4H), 1.85-1.70 (m, 4H), 1.31 (s, 9H), 1.02 (t, $^3$J=7.4 Hz, 3H), 1.01 (t, $^3$J=7.4 Hz, 3H). HRMS (ESI, acetonitrile/CHCl$_3$ 1:1, pos-mode): calcd for C$_{40}$H$_{43}$Br$_2$N$_4$O$_4$ 801.1646. Found 806.1650.

Preparation of Compound 1e

Dry DMF (7 mL) is added to a mixture of compound 3d (76.0 mg, 0.095 mmol), K$_2$CO$_3$ (26.5 mg, 0.192 mmol) und Pd(OAc)$_2$ (6.0 mg, 27 μmol) under argon. The reaction mixture is stirred at 100° C. for 90 min. After cooling of the reaction mixture to room temperature, the solvent is removed under vacuo. The residue is purified by column chromatography (dichloromethane/pentane 1/1) yielding a dark red solid (33.0 mg, 54%). $^1$H NMR (400 MHz, CD$_2$Cl$_2$): 11.11 (s, 2H), 9.44 (d, $^3$J=8.7 Hz, 2H), 7.59 (d, $^4$J=1.8 Hz, 2H), 7.50 (dd, $^3$J=8.7 Hz, $^4$J=1.8 Hz, 2H), 4.05-3.98 (m, 4H), 1.82-1.69 (m, 4H), 1.52 (s, 18H), 1.08-0.98 (m, 6H).

Example 7

Preparation of Compound 1f

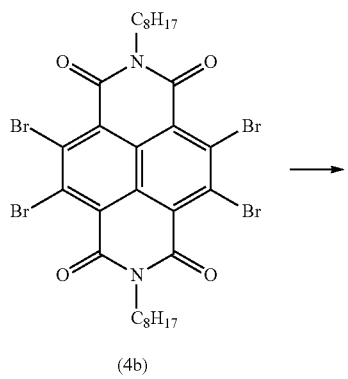

(4b)

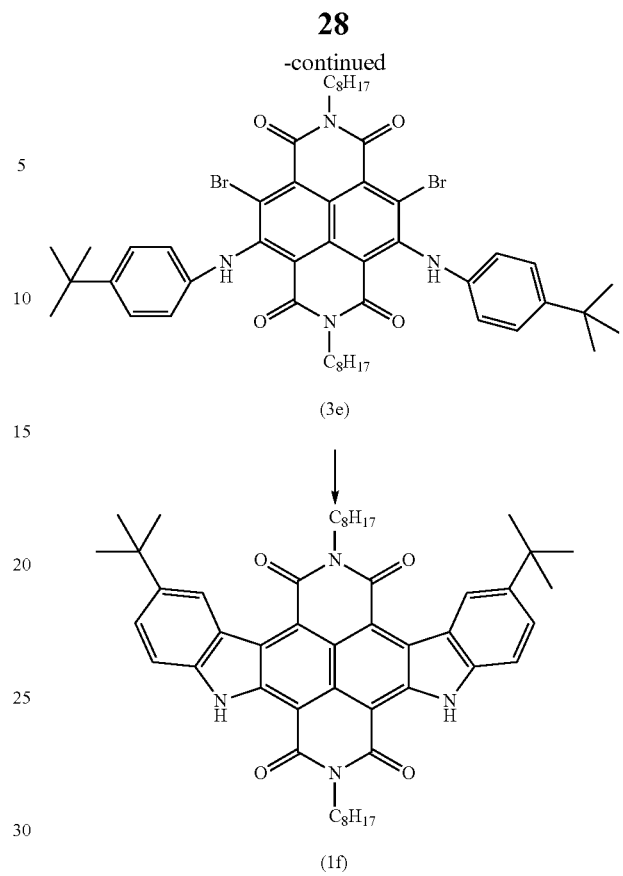

(3e)

Preparation of Compound 3e 4-tert-Butylaniline (0.1 mL, 0.63 mmol) is added to a solution of compound 4b (199 mg, 0.247 mmol) in chloroform (30 mL). The solution is heated under reflux for 3 h 15 min. The solvent is removed under reduced pressure, and the residue is purified by column chromatography (dichloromethane/pentane 1:1). A violet solid is obtained (177 mg, 76%). $^1$H NMR (400 MHz, CDCl$_3$) 12.0 (bs, 2H), 7.37-7.30 (m, 4H), 6.99-6.93 (m, 4H), 4.24-4.08 (m, 4H), 1.82-1.62 (m, 4H), 1.33 (s, 9H), 1.45-1.17 (m), 0.92-0.82 (m, 6H). HRMS (ESI, acetonitrile/CHCl$_3$ 1:1, pos-mode): calcd for C$_{50}$H$_{63}$Br$_2$N$_4$O$_4$ 941.3211. Found 941.3209.

Preparation of Compound 1f

Dry DMF (8 mL) is added to a mixture of compound 3e (160 mg, 0.170 mmol), K$_2$CO$_3$ (48 mg, 0.347 mmol) und Pd(OAc)$_2$ (11.1 mg, 49.4 μmol) under argon. The reaction mixture is stirred at 100° C. for 60 min. After cooling of the reaction mixture to room temperature, the solvent is removed under vacuo. The residue is purified by column chromatography (dichloromethane/pentane 1/1) yielding a dark red solid (42.8 mg, 32%). $^1$H NMR (400 MHz, CD$_2$Cl$_2$): 11.25 (s, 2H), 9.78 (d, $^4$J=2.0 Hz, 2H), 7.74 (dd, $^3$J=8.4 Hz, $^4$J=2.0 Hz, 2H), dd ($^3$J=8.4 Hz, $^5$J=0.5 Hz, 2H), 4.43 (t, $^3$J=7.5 Hz, 2H), 4.30 (t, $^3$J=7.5 Hz, 2H), 2.00-1.88 (m, 2H), 1.88-1.76 (m, 2H), 1.55 (s, 9H), 1.52-1.22 (m, 20H), 0.92-0.85 (m, 6H). HRMS (ESI, acetonitrile/CHCl$_3$ 1:1, pos-mode): calcd for C$_{50}$H$_{63}$Br$_2$N$_4$O$_4$ 941.3211. Found 941.3209.

Example 8

Preparation of Compound 1g

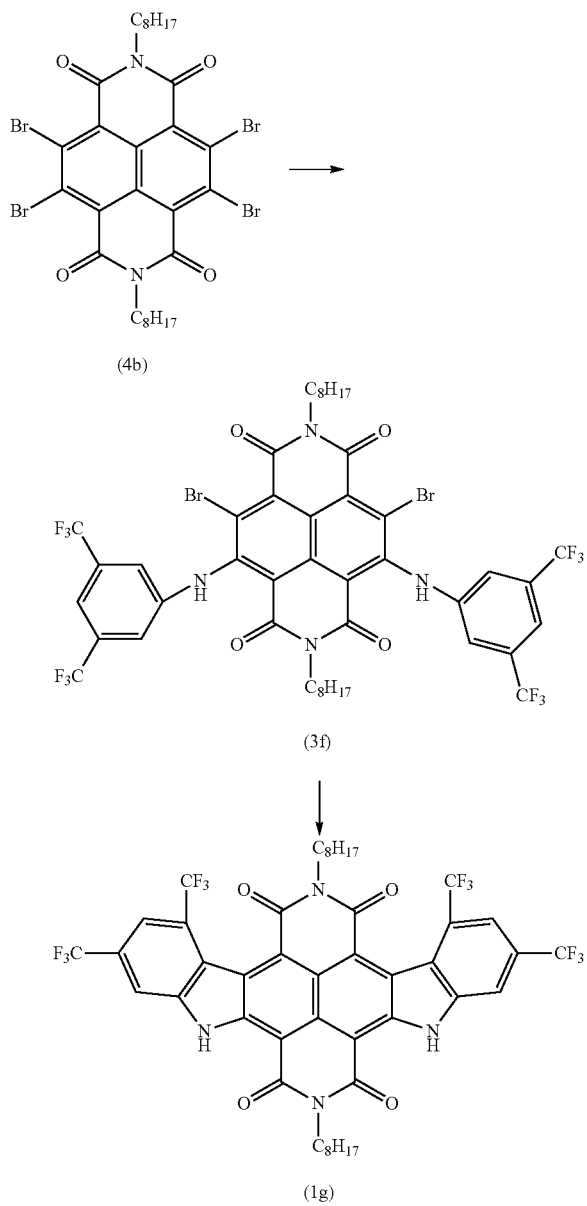

Preparation of Compound 3f

3-Bis(trifluoromethyl)aniline (0.20 mL, 1.2 mmol) is added to a solution of compound 4b (72.3 mg, 0.0898 mmol) in toluene (5 mL). After heating the solution at 70° C. for 4 days 0.1 mL 0.6 mmol) 3-bis(trifluoromethyl)aniline is added. The solution is heated at 70° C. for 2 days more. The solvent is removed under reduced pressure, and the residue is purified by column chromatography (dichloromethane/pentane 1:4). A red solid is obtained (80.6 mg, 81%). $^1$H NMR (400 MHz, CDCl$_3$): 12.00 (s, 2H), 7.63 (s, 2H), 7.38 (s, 4H), 4.26-4.17 (m, 4H), 1.82-1.68 (m, 4H), 1.47-1.19 (m, 20H), 0.92-0.81 (m, 6H). HRMS (ESI, acetonitrile/CHCl$_3$ 1:1, pos-mode): calcd for $C_{46}H_{43}Br_2F_{12}N_4O_4$ 1101.1454. Found 1101.1457.

Preparation of Compound 1g

Dry DMF (5 mL) is added to a mixture of compound 3f (83.8 mg, 0.076 mmol), K$_2$CO$_3$ (21.5 mg, 0.156 mmol) und Pd(OAc)$_2$ (5.2 mg, 23 µmol) under argon. The reaction mixture is stirred at 100° C. for 45 min, and then refluxed for 1 h. After cooling of the reaction mixture to room temperature, the solvent is removed under vacuo. The residue is purified by column chromatography (dichloromethane/pentane 1:1) yielding a dark red solid (22.8 mg, 32%). $^1$H NMR (400 MHz, CDCl$_3$): 11.3 (s, 2H), 8.03 (s, 2H), 7.92 (s, 2H), 4.36-4.25 (m, 2H), 4.21 (t, $^3$J=7.4 Hz, 2H), 2.01 (tt, $^3$J=6.8 Hz, 2H), 1.77 (tt, $^3$J=6.8 Hz, 2H), 1.62-1.18 (m, 20H), 0.93-0.83 (m, 6H). HRMS (ESI, acetonitrile/CHCl$_3$ 1:1, pos-mode): calcd for $C_{46}H_{41}F_{12}N_4O_4$ 941.2931. Found 941.2929.

Example 9

Preparation of Compound 2b

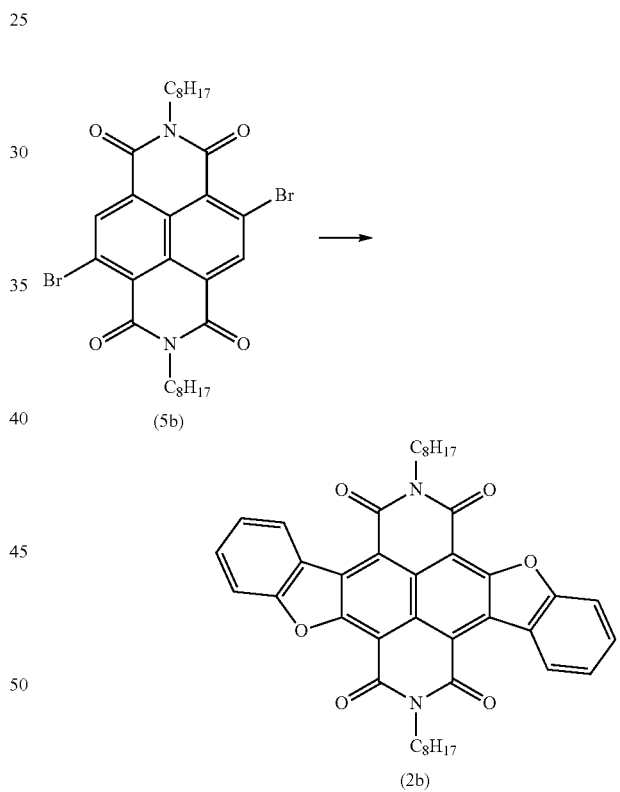

Preparation of Compound 5b

The compound 5b is prepared in analogy to 5a.

Preparation of Compound 2b

DMF (7 mL) is added to a mixture of compound 5b (180 mg, 0.278 mmol), 2-bromophenol (0.08 mL, 0.75 mmol), Pd(OAc)$_2$ (18.7 mg, 83.3 µmol) and K$_2$CO$_3$ (76.3 mg, 0.537 mmol) under argon. The reaction mixture is heated to reflux under argon for 3 hours. The solvent is removed under reduced pressure. The residue is purified by column chromatography (dichloromethane). A yellow fluorescent solid is obtained (30.1 mg, 16%). $^1$H NMR (400 MHz, CDCl$_3$): 9.61 (d, $^3$J=8.0 Hz, 2H), 7.84 (d, $^3$J=7.9 Hz, 2H), 7.76-7.72 (m, 2H), 7.56-7.50 (m, 2H), 4.35 (t, $^3$J=7.8 Hz, 4H), 1.89-1.81 (m, 2H), 1.52-1.08 (m), 0.82 (t, $^3$J=6.8 Hz, 6H).

Example 10

Method for Determining the Transistor Characteristics

Highly doped p-type silicon (100) wafers (0.01-0.02 Ω·cm) were used as substrates A. Highly doped p-type silicon (100) wafers (0.005-0.02 Ω·cm) with a 100 nm thick thermally grown SiO$_2$ layer (capacitance 34 nF/cm$^2$) were used as substrates B.

Onto substrates A, a 30 nm thick layer of aluminum is deposited by thermal evaporation in a Leybold UNIVEX 300 vacuum evaporator from a tungsten wire, at a pressure of 2×10$^{-6}$ mbar and with an evaporation rate of 1 nm/s. The surface of the aluminum layer is oxidized by a brief exposure to an oxygen plasma in an Oxford reactive ion etcher (RIE, oxygen flow rate: 30 sccm, pressure: 10 mTorr, plasma power: 200 W, plasma duration 30 sec) and the substrate is then immersed into a 2-propanol solution of a phosphonic acid (1 mMol solution of C$_{14}$H$_{29}$PO(OH)$_2$ [TDPA] or 1 mMol solution of C$_7$F$_{15}$C$_{11}$H$_{22}$PO(OH)$_2$ [FODPA]) and left in the solution for 1 hour, which results in the formation of a self-assembled monolayer (SAM) of phosphonic acid molecules on the aluminum oxide surface. The substrate is taken out of the solution and rinsed with pure 2-propanol, dried in a stream of nitrogen and left for 10 min on a hotplate at a temperature of 100° C. The total capacitance of the AlO$_x$/SAM gate dielectric on substrate A is 810 nF/cm$^2$ in case of C$_{14}$H$_{29}$PO(OH)$_2$ and 710 nF/cm$^2$ in case of C$_7$F$_{15}$C$_{11}$H$_{22}$PO(OH)$_2$.

On substrates B, an about 8 nm thick layer of Al$_2$O$_3$ is deposited by atomic layer deposition in a Cambridge NanoTech Savannah (80 cycles at a substrate temperature of 250° C.). The surface of the aluminum oxide layer is activated by a brief exposure to an oxygen plasma in an Oxford reactive ion etcher (RIE, oxygen flow rate: 30 sccm, pressure: 10 mTorr, plasma power: 200 W, plasma duration 30 sec) and the substrate is then immersed into a 2-propanol solution of a phosphonic acid (1 mMol solution of C$_{14}$H$_{29}$PO(OH)$_2$ [TDPA] or 1 mMol solution of C$_7$F$_{15}$C$_{11}$H$_{22}$PO(OH)$_2$ [FODPA]) and left in the solution for 1 hour, which results in the formation of a self-assembled monolayer (SAM) of phosphonic acid molecules on the aluminum oxide surface. The substrate is taken out of the solution and rinsed with pure 2-propanol, dried in a stream of nitrogen and left for 10 min on a hotplate at a temperature of 100° C. The total capacitance of the SiO$_2$/AlO$_x$/SAM gate dielectric on substrate B is 32 nF/cm$^2$ (independent on the choice of the phosphonic acid).

The contact angle of water on the TDPA-treated substrates is 108°, and on the FODPA-treated substrates 118°.

A 30 nm thick film of compounds of the present invention as organic semiconductor is deposited by thermal sublimation in a Leybold UNIVEX 300 vacuum evaporator from a molybdenum boat, at a pressure of 2×10$^{-6}$ mbar and with an evaporation rate of 0.3 nm/s.

For the source and drain contacts 30 nm of gold is evaporated through a shadow mask in a Leybold UNIVEX 300 vacuum evaporator from tungsten boat, at a pressure of 2×10$^{-6}$ mbar and with an evaporation rate of 0.3 nm/s. The transistors have a channel length (L) ranging from 10 to 100 μm and a channel width (W) ranging from 50 to 1000 μm.

To be able to contact the back side of the silicon wafer, the wafer (which also serves as the gate electrode of the transistors) is scratched on the back side and coated with silver ink.

The electrical characteristics of the transistors are measured on a Micromanipulator 6200 probe station using an Agilent 4156C semiconductor parameter analyzer. All measurements are performed in air at room temperature. The probe needles are brought into contact with the source and drain contacts of the transistors by putting them down carefully on top of the gold contacts. The gate electrode is contacted through the metal substrate holder onto which the wafer is placed during the measurements.

To obtain the transfer curve the drain-source voltage (V$_{DS}$) is held to 3 V (in case of substrate A) or 40 V (in case of substrate B). The gate-source voltage V$_{GS}$ is swept at medium speed from 0 to 3 V in steps of 0.03 V (substrate A) or from 0 to 40 V in steps of 0.4 V (substrate B) and back. The charge-carrier mobility is extracted in the saturation regime from the slope of (I$_D$)$^{1/2}$ versus V$_{GS}$.

To obtain the output characteristics the drain-source voltage (V$_{DS}$) is swept at medium speed from 0 to 3 V in steps of 0.03 V (substrate A) and from 0 to 40 V in steps of 0.4 V (substrate B), while the gate-source voltage V$_{GS}$ is held at up to 8 different voltages (e.g. 0, 0.5, 1, 1.5, 2, 2.5, 3 V in case of substrate A or 0, 10, 20, 30, 40 V in case of substrate B).

The results are depicted in Table 1.

TABLE 1

| Organic Semiconductor | Substrate | SAM | Substrate Temperature T$_{sub}$ [° C.] | Hole Mobility μ$_p$ [cm$^2$/Vs] | Electron Mobility μ$_e$ [cm$^2$/Vs] | On/Off Ratio I$_{on}$/I$_{off}$ |
|---|---|---|---|---|---|---|
| 1a | B | FODPA | 100 | 0.2 | 0.006 | 7 × 10$^5$/10$^4$ |
| 1a | A | FODPA | 100 | 0.02 | 0.003 | 5 × 10$^5$/3 × 10$^2$ |
| 1a | A | TDPA | 100 | | 0.003 | 2 × 10$^4$ |
| 1b | B | FODPA | 100 | 0.0001 | | 2 × 10$^4$ |
| 1b | B | TDPA | 100 | 0.0001 | | 10$^4$ |
| 1b | A | FODPA | 100 | 0.0001 | | 10$^2$ |
| 1b | A | TDPA | 100 | | 0.0003 | 3 × 10$^3$ |
| 1c | B | FODPA | 100 | 0.007 | | 2 × 10$^4$ |
| 1d | B | TDPA | 100 | 0.0019 | | 10$^4$ |
| 1d | A | TDPA | 100 | 0.0029 | | 3 × 10$^3$ |
| 1e | B | FODPA | 100 | 0.03 | | 10$^4$ |
| 1e | B | TDPA | 100 | 0.002 | | 10$^5$ |
| 1f | B | FODPA | 100 | 0.07 | | 10$^5$ |
| 1f | B | TDPA | 100 | 0.00064 | | 10$^3$ |
| 1f | A | FODPA | 100 | 0.02 | | 2 × 10$^5$ |
| 1g | B | FODPA | 100 | | 0.0008 | 3 × 10$^2$ |
| 1g | B | TDPA | 100 | | 0.0002 | 3 × 10$^2$ |
| 2a | B | FODPA | 100 | | 0.0038 | 10$^4$ |
| 2a | B | TDPA | 100 | | 0.06 | 10$^7$ |
| 2a | A | FODPA | 100 | | 0.0012 | 5 × 10$^2$ |
| 2a | A | TDPA | 100 | | 0.03 | 5 × 10$^5$ |
| 2b | B | FODPA | 100 | 0.006 | 0.02 | 2 × 10$^3$/10$^4$ |
| 2b | B | TDPA | 100 | | 0.006 | 10$^5$ |

The invention claimed is:
1. A compound of the formula (1) or (2)

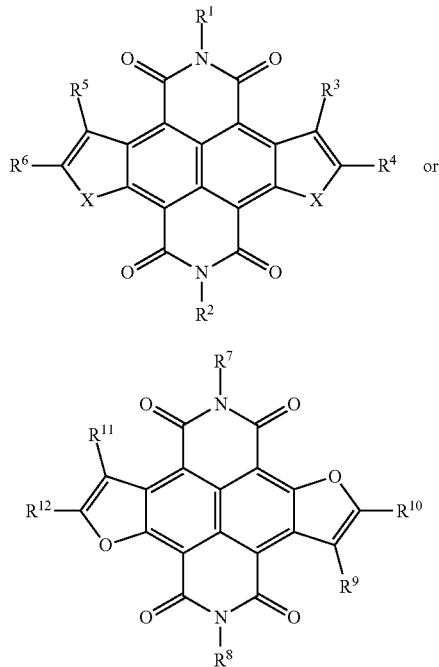

wherein
X is O or NR$^{13}$,
wherein R$^{13}$ is H, C$_{1-30}$-alkyl, C$_{3-8}$-cycloalkyl, C$_{6-14}$-aryl or a 5 to 14 membered heterocyclic system A,
R$^1$, R$^2$, R$^7$ and R$^8$ are independently from each other H, C$_{1-30}$-alkyl, C$_{3-8}$-cycloalkyl, C$_{6-14}$-aryl or a 5 to 14 membered heterocyclic system A, and
R$^3$, R$^4$, R$^5$, R$^6$, R$^9$, R$^{10}$, R$^{11}$ and R$^{12}$ are independently from each other H, C$_{1-30}$-alkyl, C$_{3-8}$-cycloalkyl, C$_{6-14}$-aryl, a 5 to 14 membered heterocyclic system A, halogen, NR$^{14}$R$^{15}$, OH, OR$^{16}$, SH, SR$^{17}$, CN, NO$_2$, —S—CN, —C(O)—H, —C(O)—R$^{18}$, COOH, —C(O)—NR$^{19}$R$^{20}$, —SO$_2$—OH, —SO$_2$—NH$_2$ or —SO$_2$—R$^{21}$, wherein
R$^{14}$, R$^{15}$, R$^{16}$, R$^{17}$, R$^{18}$, R$^{19}$, R$^{20}$ and R$^{21}$ are independently from each other H, C$_{1-30}$-alkyl, C$_{3-8}$-cycloalkyl, C$_{6-14}$-aryl or a 5 to 14 membered heterocyclic system A,
or
R$^3$ and R$^4$,
R$^5$ and R$^6$,
R$^9$ and R$^{10}$, or
R$^{11}$ and R$^{12}$
together with the C-atoms, to which they are attached, form a C$_{5-14}$-membered ring system or a 5 to 14 membered heterocyclic system B,
wherein
C$_{1-30}$-alkyl is optionally substituted with one or more substituents selected from the group consisting of —O—C$_{1-10}$-alkyl, —[—O—C$_{1-6}$-alkylene-]$_n$-O—C$_{1-10}$-alkyl, phenyl, cyclopentyl, cyclohexyl, halogen, —C(O)O—R$^{22}$, —O—C(O)—R$^{23}$ and C(O)—R$^{24}$,
C$_{3-8}$-cycloalkyl is optionally substituted with one or more substituents selected from the group consisting of C$_{1-10}$-alkyl, —O—C$_{1-10}$-alkyl, —[—O—C$_{1-6}$-alkylene-]$_n$-O—C$_{1-10}$-alkyl and phenyl,
C$_{6-14}$-aryl, the C$_{5-14}$-membered ring system, the 5 to 14 membered heterocyclic system A and the 5 to 14 membered heterocyclic system B is optionally substituted with one or more substituents selected from the group consisting of C$_{1-10}$-alkyl, —O—C$_{1-10}$-alkyl, —[—O—C$_{1-6}$-alkylene-]$_n$—O—C$_{1-10}$-alkyl, cyclopentyl, cyclohexyl, phenyl, halogen, CN, NO$_2$, —S—CN, —C(O)—H, —C(O)O—R$^{22}$, —O—C(O)—R$^{23}$ and C(O)—R$^{24}$,
wherein
C$_{1-10}$-alkyl is optionally substituted with one or more halogen,
R$^{22}$, R$^{23}$ and R$^{24}$ are independently from each other C$_{1-10}$-alkyl, cyclopentyl, cyclohexyl or phenyl, and
n is 1 to 15 and
wherein the heterocyclic system A is monocyclic or polycyclic and the heterocyclic system B is monocyclic or polycyclic.

2. The compound of claim 1, wherein
X is O or NR$^{13}$,
wherein R$^{13}$ is H or C$_{1-30}$-alkyl,
R$^1$, R$^2$, R$^7$ and R$^8$ are independently from each other H, C$_{1-30}$-alkyl or C$_{6-14}$-aryl, and
R$^3$ and R$^4$,
R$^5$ and R$^6$,
R$^9$ and R$^{10}$, or
R$^{11}$ and R$^{12}$
together with the C-atoms, to which they are attached, form a C$_{5-14}$-membered ring system or a 5 to 14 membered heterocyclic system B,
wherein
C$_{1-30}$-alkyl is optionally substituted with one or more substituents selected from the group consisting of —O—C$_{1-10}$-alkyl, —[—O—C$_{1-6}$-alkylene-]$_n$-O—C$_{1-10}$-alkyl, phenyl, cyclopentyl, cyclohexyl, halogen, —C(O)O—R$^{22}$, —O—C(O)—R$^{23}$ and C(O)—R$^{24}$,
C$_{6-14}$-aryl, the C$_{5-14}$-membered ring system and the 5 to 14 membered heterocyclic system B is optionally substituted with one or more substituents selected from the group consisting of C$_{1-10}$-alkyl, —O—C$_{1-10}$-alkyl, —[—O—C$_{1-6}$-alkylene-]$_n$-O—C$_{1-10}$-alkyl, cyclopentyl, cyclohexyl, phenyl, halogen, CN, NO$_2$, —S—CN, —C(O)—H, —C(O)O—R$^{22}$, —O—C(O)—R$^{23}$ and C(O)—R$^{24}$,
wherein
C$_{1-10}$-alkyl is optionally substituted with one or more halogen,
R$^{22}$, R$^{23}$ and R$^{24}$ are independently from each other C$_{1-10}$-alkyl, cyclopentyl, cyclohexyl or phenyl, and
n is 1 to 15.

3. The compound of claim 1, wherein
X is O or NR$^{13}$,
wherein R$^{13}$ is H,
R$^1$, R$^2$, R$^7$ and R$^8$ are independently from each other C$_{1-20}$-alkyl or C$_{6-14}$-aryl, and
R$^3$ and R$^4$,
R$^5$ and R$^6$,
R$^9$ and R$^{10}$, or
R$^{11}$ and R$^{12}$
together with the C-atoms, to which they are attached, form a C$_{5-14}$-membered ring system
wherein
C$_{1-20}$-alkyl is optionally substituted with one or more substituents selected from the group consisting of —O—C$_{1-10}$-alkyl, —[—O—C$_{1-6}$-alkylene-]$_n$-O—C$_{1-10}$-alkyl, phenyl, cyclopentyl, cyclohexyl, halogen, —C(O)O—R$^{22}$, —O—C(O)—R$^{23}$ and C(O)—R$^{24}$, C$_{6-14}$-aryl and the C$_{5-14}$-membered ring system is optionally substituted with one or more substituents selected from the group consisting of C$_{1-10}$-alkyl, —O—C$_{1-10}$-alkyl, —[—O—C$_{1-6}$-alkylene-]$_n$-O—C$_{1-10}$-alkyl, cyclopentyl, cyclohexyl, phenyl, halogen, CN, NO$_2$, —S—CN, —C(O)—H, —C(O)O—R$^{22}$, —O—C(O)—R$^{23}$ and C(O)—R$^{24}$, wherein C$_{1-10}$-alkyl is optionally substituted with one or more halogen, R$^{22}$, R$^{23}$ and R$^{24}$ are independently from each other C$_{1-10}$-alkyl, cyclopentyl, cyclohexyl or phenyl, and n is 1 to 15.

4. The compound of claim 1, wherein

X is O or NR$^{13}$, wherein R$^{13}$ is H,

R$^1$, R$^2$, R$^7$ and R$^8$ are independently from each other C$_{1-20}$-alkyl or C$_{6-14}$-aryl, and R$^3$ and R$^4$, R$^5$ and R$^6$, R$^9$ and R$^{10}$, or R$^{11}$ and R$^{12}$ together with the C-atoms, to which they are attached, form a C$_{5-14}$-membered ring system selected from the group consisting of

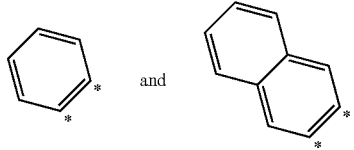

wherein the C-atoms marked with a star are the C-atoms to which R$^3$ and R$^4$, R$^5$ and R$^6$, R$^9$ and R$^{10}$, or R$^{11}$ and R$^{12}$ are attached, wherein C$_{6-14}$-aryl and the C$_{5-14}$-membered ring system selected from the group consisting of

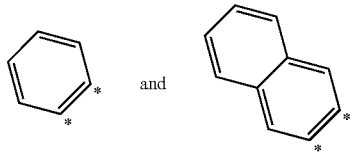

is optionally substituted with one or more substituents selected from the group consisting of C$_{1-10}$-alkyl.

5. An electronic device comprising the compounds of claim 1.

6. The electronic device of claim 5, wherein the electronic device is an organic field effect transistor.

7. A semiconducting material comprising the compound as claimed in claim 1.

8. The compound of claim 1, wherein the heterocyclic system A is selected from the group consisting of

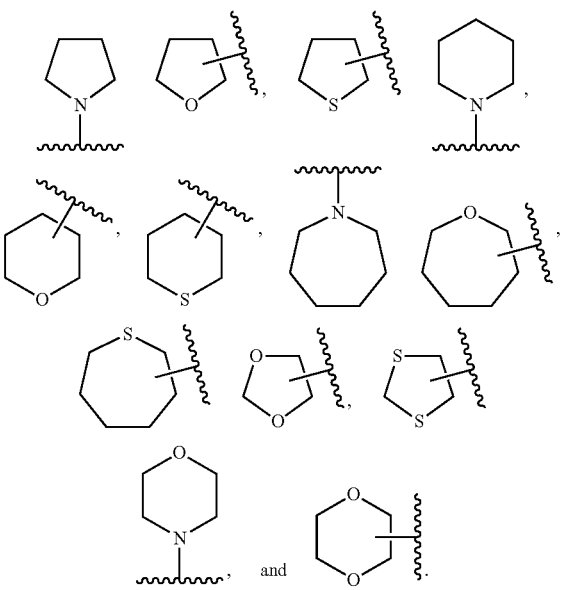

9. The compound of claim 1, wherein the heterocyclic system A is selected from the group consisting of

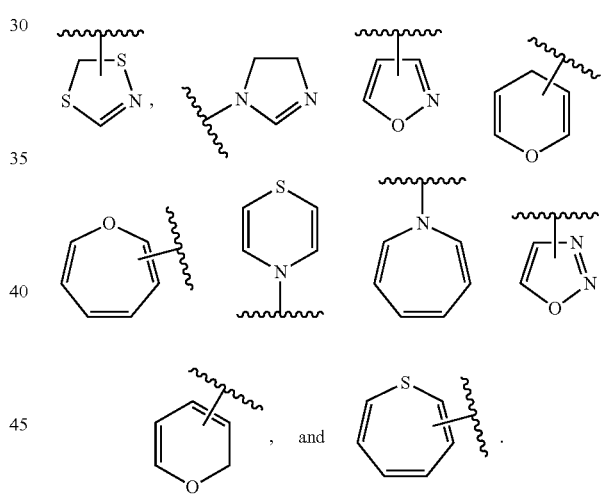

10. The compound of claim 1, wherein the heterocyclic system A is selected from the group consisting of

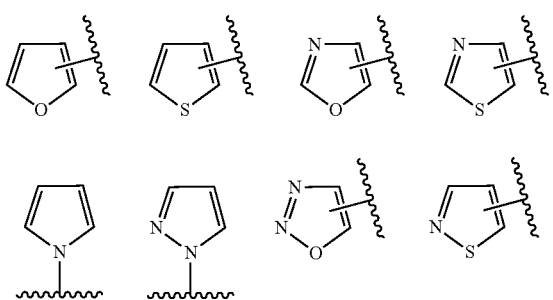

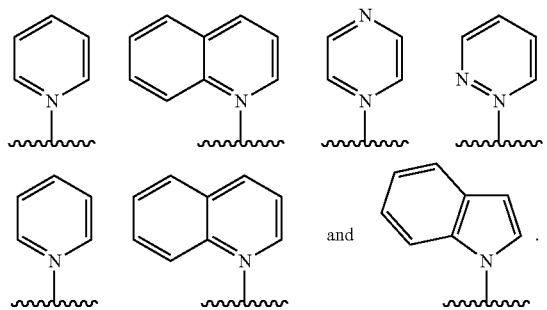

11. The compound of claim 1, wherein the C5-14-membered ring system is selected from the group consisting of

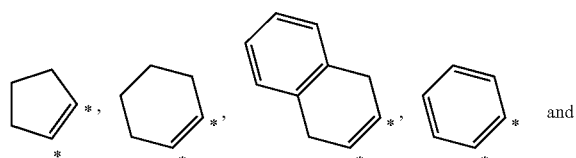

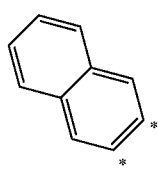

wherein the C-atoms marked with a star are the C-atoms to which $R^3$ and $R^4$, $R^5$ and $R^6$, $R^9$ and $R^{10}$, or $R^{11}$ and $R^{12}$ are attached.

12. The compound of claim 1, wherein the heterocyclic system B is selected from the group consisting of

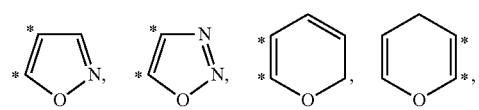

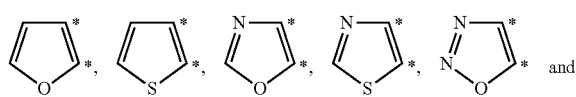

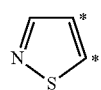

wherein the C-atoms marked with a star are the C-atoms to which $R^3$ and $R^4$, $R^5$ and $R^6$, $R^9$ and $R^{10}$, or $R^{11}$ and $R^{12}$ are attached.

13. The compound of claim 1, wherein the compound is selected from the group consisting of

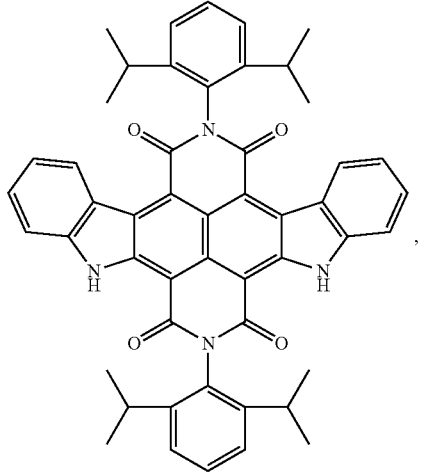
(1a)

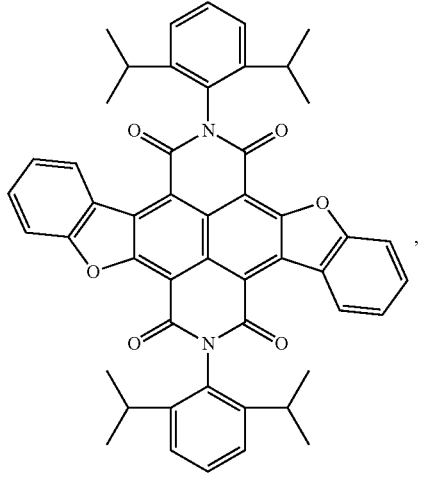
(2a)

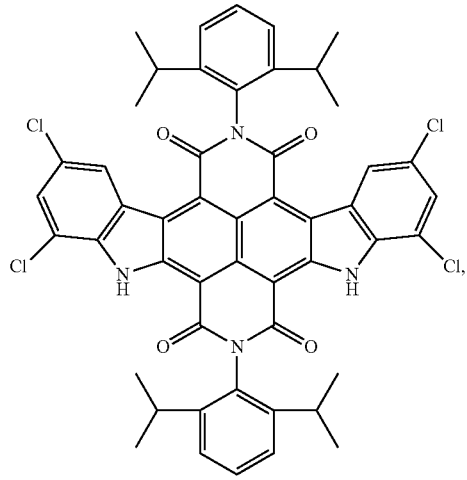
(1b)

-continued

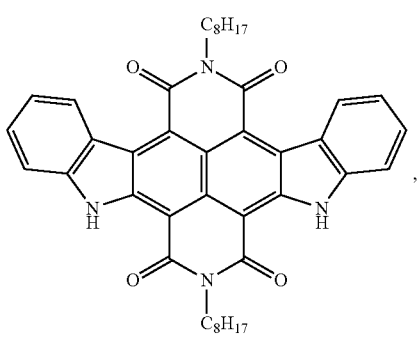
(1c)

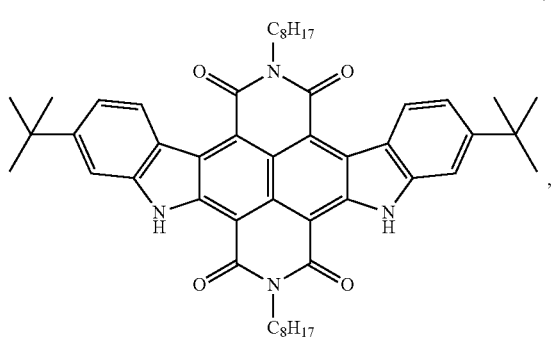
(1d)

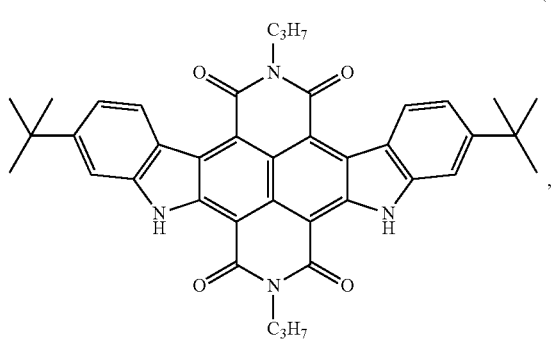
(1e)

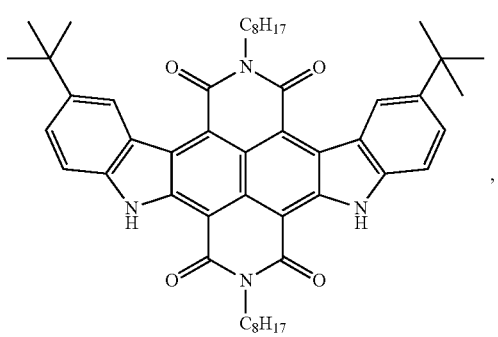
(1f)

-continued (1g)

(2b)

14. The compound of claim 1, wherein
X is O or NR$^{13}$,
wherein R$^{13}$ is H,
R$^1$, R$^2$, R$^7$ and R$^8$ are independently from each other C$_{1-20}$-alkyl or C$_{6-14}$-aryl, and
R$^3$ and R$^4$,
R$^5$ and R$^6$,
R$^9$ and R$^{10}$, or
R$^{11}$ and R$^{12}$
together with the C-atoms, to which they are attached, form a C$_{5-14}$-membered ring system selected from the group consisting of

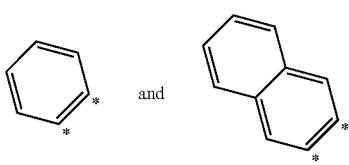

wherein the C-atoms marked with a star are the C-atoms to which R$^3$ and R$^4$, R$^5$ and R$^6$, R$^9$ and R$^{10}$, or R$^{11}$ and R$^{12}$ are attached,
wherein
the C$_{5-14}$-membered ring system selected from the group consisting of

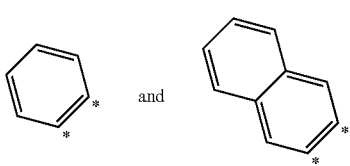

is optionally substituted with one or more substituents selected from the group consisting of $C_{1-10}$-alkyl, which is substituted with one or more halogens.

* * * * *